(12) United States Patent
Lin et al.

(10) Patent No.: US 10,533,939 B2
(45) Date of Patent: *Jan. 14, 2020

(54) GAS DETECTION DEVICE

(71) Applicant: RADIANT INNOVATION INC., Hsinchu (TW)

(72) Inventors: Tseng-Lung Lin, Hsinchu (TW); Shao-Yun Yu, Hsinchu (TW); Yu-Chien Huang, Hsinchu (TW)

(73) Assignee: RADIANT INNOVATION INC., Hsinchu (TW)

( * ) Notice: Subject to any disclaimer, the term of this patent is extended or adjusted under 35 U.S.C. 154(b) by 221 days.

This patent is subject to a terminal disclaimer.

(21) Appl. No.: 15/809,906

(22) Filed: Nov. 10, 2017

(65) Prior Publication Data

US 2019/0145828 A1 May 16, 2019

(51) Int. Cl.
| | |
|---|---|
| *G01N 21/3504* | (2014.01) |
| *G01N 21/03* | (2006.01) |
| *G01J 1/04* | (2006.01) |
| *G01N 21/31* | (2006.01) |

(52) U.S. Cl.
CPC ........ *G01N 21/3504* (2013.01); *G01J 1/0422* (2013.01); *G01N 21/0303* (2013.01); *G01J 2001/0481* (2013.01); *G01N 21/314* (2013.01)

(58) Field of Classification Search
CPC .... G01J 5/0014; G01J 5/0809; G01J 21/0303; G01J 21/3504; G01J 21/314; G01J 1/0422; G01J 2001/0481
See application file for complete search history.

(56) References Cited

U.S. PATENT DOCUMENTS

| | | | | |
|---|---|---|---|---|
| 4,618,771 A | * | 10/1986 | Farren | G01N 21/37 250/343 |
| 4,808,825 A | * | 2/1989 | Miyatake | G01J 3/108 250/343 |
| 6,120,166 A | * | 9/2000 | Price | G01J 3/10 362/302 |
| 2014/0367574 A1 | * | 12/2014 | Lin | G01N 21/3504 250/343 |
| 2015/0129770 A1 | * | 5/2015 | Henderson | G01N 21/3504 250/343 |

\* cited by examiner

*Primary Examiner* — David P Porta
*Assistant Examiner* — Jeremy S Valentiner
(74) *Attorney, Agent, or Firm* — Li & Cai Intellectual Property (USA) Office

(57) ABSTRACT

The instant disclosure provides a gas detection device including a chamber module, a light emitting module and an optical sensing module. The chamber module includes a condensing chamber, a receiving chamber and a sampling chamber. The condensing chamber has a first reflecting structure, a second reflecting structure and a third reflecting structure. The first reflecting structure is disposed between the second reflecting structure and the third reflecting structure. The light emitting module is disposed on the condensing chamber and includes a light emitting unit corresponding to the condensing chamber. The optical sensing module includes an optical sensing unit disposed in the receiving chamber.

13 Claims, 30 Drawing Sheets

GAS DETECTION DEVICE

BACKGROUND

1. Technical Field

The instant disclosure relates to a gas detection device, and in particular, to a gas detection device for measuring the concentration of gas.

2. Description of Related Art

Carbon dioxide detection devices or carbon dioxide analyzing instruments on the market generally employ non-dispersive infrared (NDIR) absorption to detect the concentration of the gas. The NDIR mainly uses a calculation based on the Beer-Lambert law. The principle of such analysis is to detect the concentration of a specific gas by using the absorption property of the gas toward infrared light having a specific wavelength and the fact that the gas concentration is proportional to the absorption quantity. For example, carbon monoxide has the strongest absorption at a wavelength of 4.7 micron ($\mu m$) and carbon dioxide has the strongest absorption at a wavelength of 4.3 micron ($\mu m$).

However, the accuracy of the gas concentration detecting devices is limited to the structure of the gas sampling chamber, and hence, the amount of the infrared light projected onto the infrared sensor is decreased and the accuracy of the detection is reduced.

In addition, Taiwanese Patent No. M476923 entitled "High Efficiency Non-dispersive Infrared Gas Chamber" utilizes the bifocal property of an ellipse and disposes the infrared light source at one of the focal points and the infrared sensor at the other focal point, thereby obtaining a high light condensation property and fulfilling the requirement of narrow incident angle of the infrared sensor. However, Taiwanese Patent No. M476923 increases the length of the infrared gas chamber body 200 by utilizing the bifocal property of an ellipse. Furthermore, the infrared sensor may not be on the correct focal point due to deviation in the assembling process and hence, the signal received by the infrared sensor is decreased.

Moreover, regarding conventional infrared light sensors, when the incident angle of the incident light is larger than 20 degrees, the filter peak will shift toward a short wavelength for about 40 nm (nanometer) due to the wave band width of the filter. Therefore, a part of the light which is not absorbed by the gas to be measured projects on the infrared sensor, and another part of the light which is related to the gas concentration to be measured is blocked from the light sensor and hence, the signal intensity is decreased and the measurement accuracy is reduced.

SUMMARY

In order to solve the problems mentioned above, the instant disclosure provides a gas detection device.

An embodiment of the instant disclosure provides a gas detection device including a chamber module, a receiving chamber, a light emitting module and an optical sensing module. The chamber module includes a condensing chamber, a receiving chamber and a sampling chamber connected between the condensing chamber and the receiving chamber, in which the condensing chamber has a first reflecting structure, a second reflecting structure connected to the first reflecting structure, and a third reflecting structure connected to the first reflecting structure. The first reflecting structure is disposed between the second reflecting structure and the third reflected structure. The light emitting module is disposed on the condensing chamber and includes a light emitting unit. The light emitting unit corresponds to the condensing chamber. The optical sensing module includes an optical sensing unit disposed in the receiving chamber.

One of the advantages of the instant disclosure is that the gas detection device includes the technical features of "the condensing chamber has a first reflecting structure, a second reflecting structure connected to the first reflecting structure, and a third reflecting structure connected to the first reflecting structure, in which the first reflecting structure is disposed between the second reflecting structure and the third reflected structure", and hence, the light-condensing efficiency of the chamber module can be increased, and the size of the gas detection device can be reduced.

In order to further understand the techniques, means and effects of the instant disclosure, the following detailed descriptions and appended drawings are hereby referred to, such that, and through which, the purposes, features and aspects of the instant disclosure can be thoroughly and concretely appreciated; however, the appended drawings are merely provided for reference and illustration, without any intention to be used for limiting the instant disclosure.

BRIEF DESCRIPTION OF THE DRAWINGS

The accompanying drawings are included to provide a further understanding of the instant disclosure, and are incorporated in and constitute a part of this specification. The drawings illustrate exemplary embodiments of the instant disclosure and, together with the description, serve to explain the principles of the instant disclosure.

DESCRIPTION OF THE EXEMPLARY EMBODIMENTS

Figure 1:
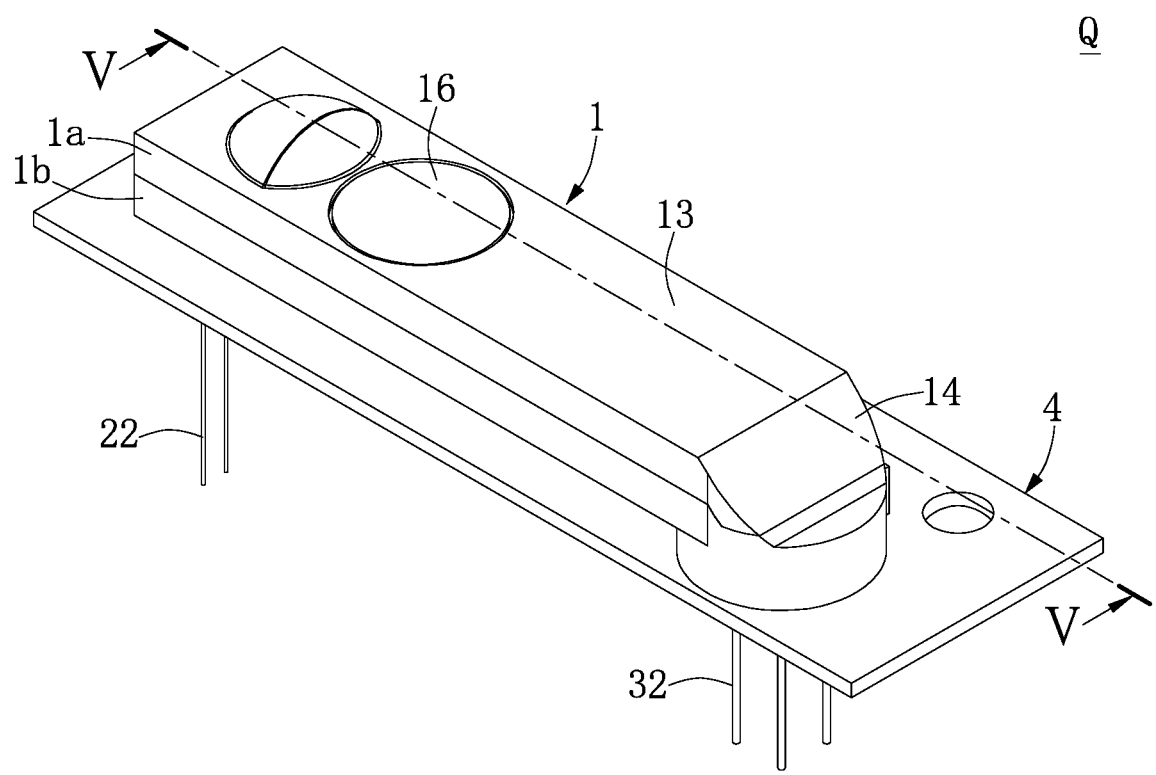
FIG. 1 is an assembly schematic view of a gas detection device according to a first embodiment of the instant disclosure.
Figure 2:
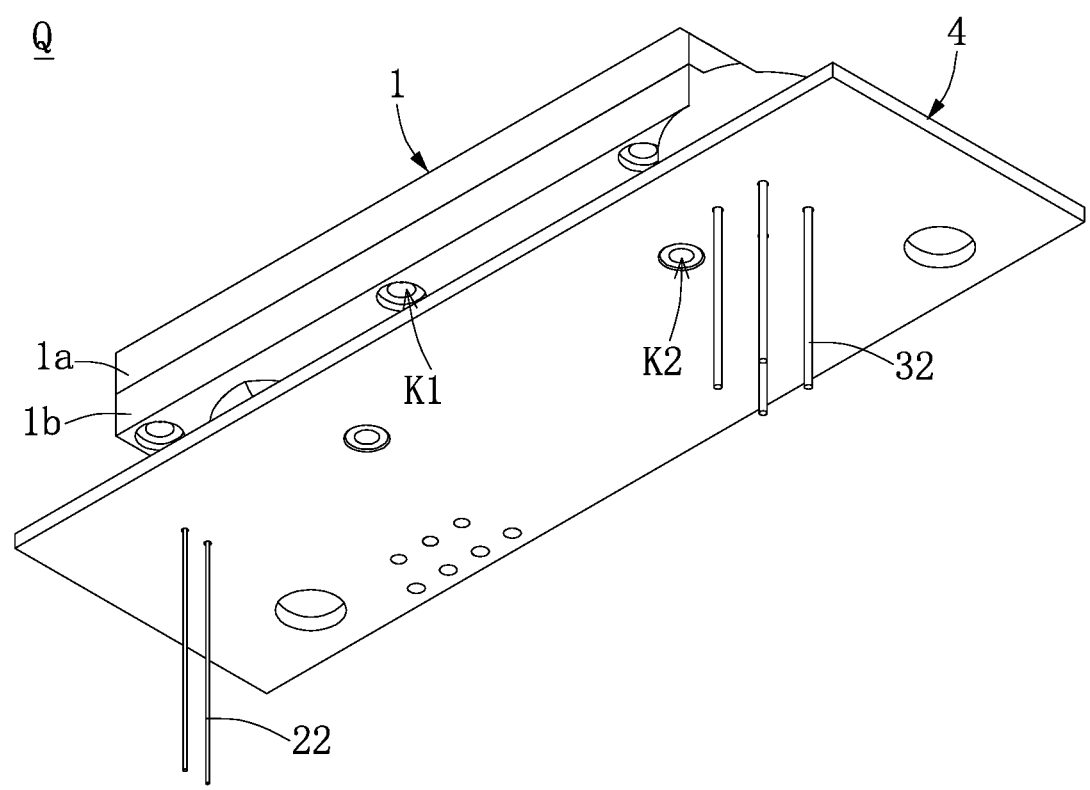
FIG. 2 is another assembly schematic view of the gas detection device according to the first embodiment of the instant disclosure.

Reference will now be made in detail to the exemplary embodiments of the instant disclosure, examples of which are illustrated in the accompanying drawings. Wherever possible, the same reference numbers are used in the drawings and the description to refer to the same or like parts.

It should be noted that the following description uses the terms "first", "second", "third", etc. to describe various elements and signals. However, the elements and signals should not be limited by these terms. These terms are only use to distinguish one element or signal from another one. In addition, the term "or" can include one or more listed element based on actual implementation.

First Embodiment

Reference is made to FIG. 1 to FIG. 4. The first embodiment of the instant disclosure provides a gas detection device Q including a chamber module 1, a light emitting module 2, an optical sensing module 3 and a substrate module 4. The light emitting module 2 and the optical sensing module 3 can be electrically connected to the substrate module 4. In addition, the substrate module 4 can be electrically connected to a display unit (not shown), a control unit (not shown) and a processing unit (not shown). For example, the light emitting module 2 is an infrared light emitter generating infrared light and the optical sensing module 3 is an infrared light sensor such as a single-channel infrared light sensor or a double-channel infrared light sensor (in which one of the infrared light collecting windows is used to detect the gas concentration and the other is used to detect the aging of the infrared light source, and the two windows can calibrate each other). However, the instant disclosure is not limited thereto.

The gas detection device Q provided by the embodiments of the instant disclosure can detect the concentration or other properties of the gas to be detected. The gas to be detected can be carbon dioxide, carbon monoxide or the combination thereof. The instant disclosure is not limited thereto. Based on the selection of different light emitting modules 2 and optical sensing modules 3, different gases can be measured. For example, regarding the detection of concentration, different types of gases can be detected by changing the wavelength filter (the filter plate) on the optical sensing module 3.

Figure 5:
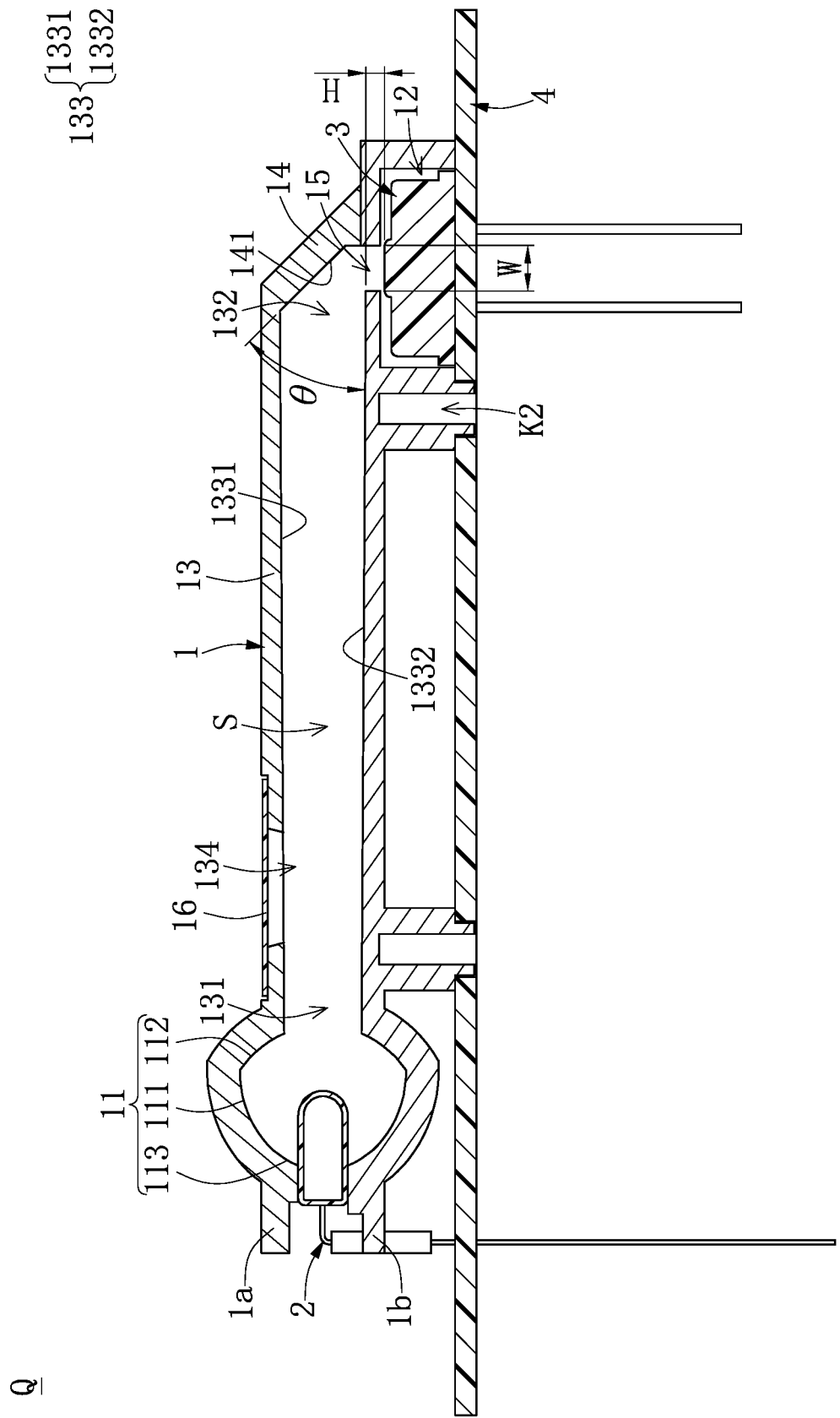
FIG. 5 is a sectional schematic view taken along line V-V in FIG. 1.
Figure 6:
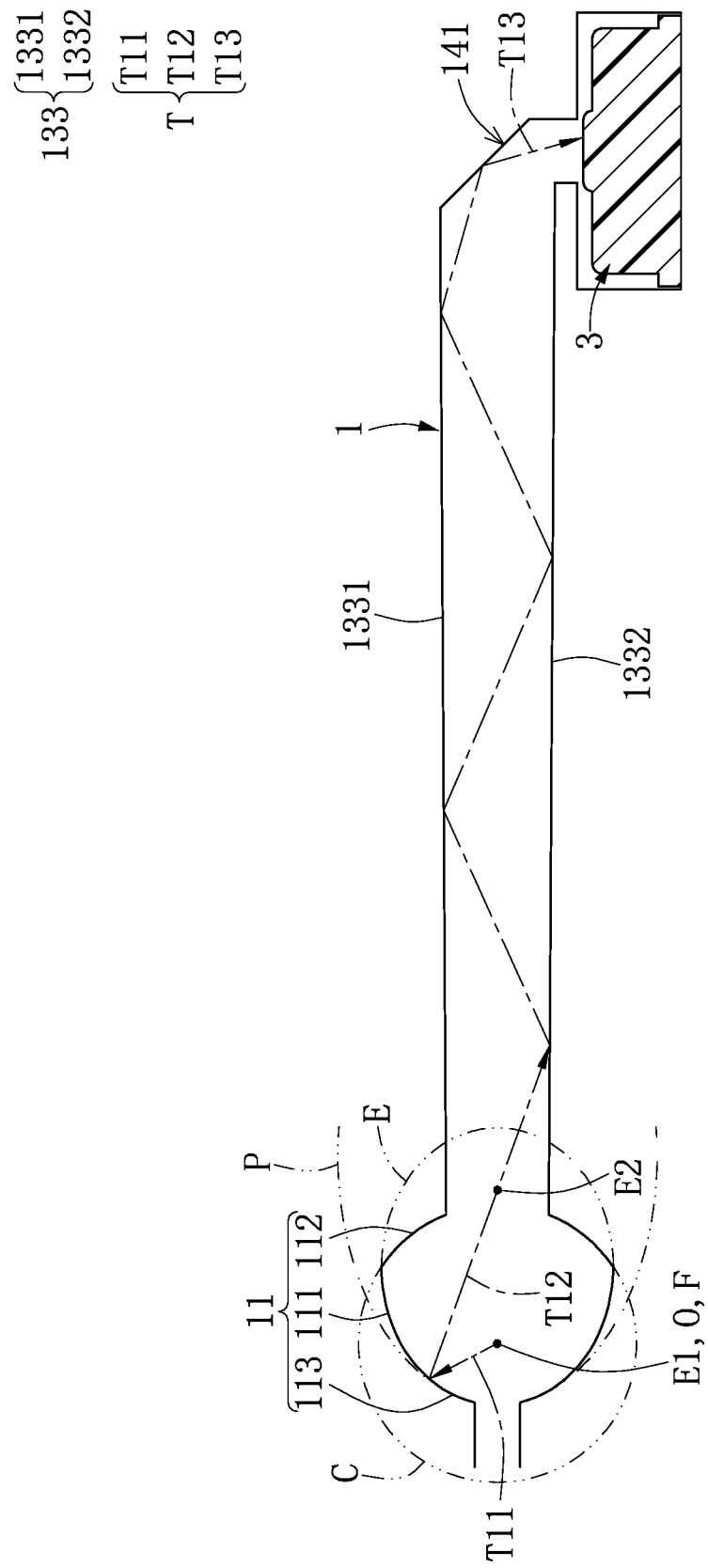
FIG. 6 depicts a path of a projection of light generated by a first reflecting structure of the gas detection device according to the first embodiment of the instant disclosure.

Reference is made to FIG. 5 and FIG. 6. The chamber module 1 has a sampling space S, and the chamber module 1 includes a condensing chamber 11, a receiving chamber 12 and a sampling chamber 13 connecting the condensing chamber 11 and the receiving chamber 12. The light emitting module 2 is disposed on the condensing chamber 11 for generating a light T, e.g., an infrared light. The optical sensing module 3 includes an optical sensing unit 31 disposed in the receiving chamber 12 for receiving the light T generated by the light emitting unit 21.

In addition, as shown in FIG. 1 to FIG. 4, the chamber module 1 includes the upper chamber module 1a and the lower chamber module 1b for facilitating the assembly of the chamber module 1. For example, the upper chamber module 1a and the lower chamber module 1b can be assembled with each other by fixing members (not shown), such as screws, in the fixing holes K1. The chamber module 1 can also be fixed on the substrate module 4 by fixing the chamber module 1 through fixing members (not shown) into the fixing holes K2. In the embodiments of the instant disclosure, the substrate module 4 can be a printed circuit board (i.e., a PCB), the light emitting module 2 can further include a connecting line 22, and the optical sensing module 3 can further include a connecting line 32. The connecting line 22 of the light emitting module 2 and the connecting line 32 of the optical sensing module 3 can stably fix the light emitting unit 21 and the optical sensing unit 31 on the substrate module 4 by soldering, thereby preventing external forces from causing loose contact.

As shown in FIG. 5, the sampling space S in the sampling chamber 13 can have a rectangular shape. However, the instant disclosure is not limited thereto. The inner surface 133 of the sampling chamber 13 (the surfaces inside of the sampling chamber 13) can have a reflecting layer (not shown). The reflecting layer can be formed in the sampling chamber 13 by metal plating or plastic plating processes. The reflecting layer is made of gold, nickel or the combination thereof. Therefore, the sampling chamber 13 having a rectangular shape is a rectangular optical integrator in which the light T generated by the light emitting module 2 is repeatedly reflected in the sampling chamber 13, and the light intensity is integrated in the sampling chamber 13, thereby forming a uniform light distribution.

As shown in FIG. 1 to FIG. 5, the sampling chamber 13 includes a first opening 131, a second opening 132 corresponding to the first opening 131, a first surface 1331, and a second surface 1332 corresponding to the first surface 1331. The first opening 131 is connected to the condensing chamber 11, the second opening 132 is connected to the receiving chamber 12, and the first surface 1331 and the second surface 1332 are disposed between the first opening 131 and the second opening 132. In addition, the first surface 1331 and the second surface 1332 can be arranged to be facing each other. The sampling chamber 13 further includes a third surface (not labeled) and a fourth surface (not labeled) corresponding to the third surface. The third surface and the fourth surface can be arranged to be facing each other. In other words, the first surface 1331 and the second surface 1332 are the upper surface and the lower surface of the sampling chamber 13, respectively, and the third surface and the fourth surface are the left and right side surfaces of the sampling chamber 13, respectively.

The sampling chamber 13 further includes one or more gas diffusion slots 134 vertically penetrating the first surface 1331 or the second surface 1332 of the sampling chamber 13. In addition, the gas diffusion slot 134 has a rectangular shape. As shown in FIG. 5, the cross section of the gas diffusion slot 134 can have a V shape. Therefore, according to the Bernoulli's principle, when the gas to be detected flows through the gas diffusion slot 134 having a V-shape cross section, the flow speed of the gas increases, and hence, the measuring time can be reduced. Furthermore, the chamber module 1 further includes a gas filtering film 16 disposed on the gas diffusion slot 134. The gas filtering film 16 can be a moisture resistant and air permeable film for preventing the suspended particles in the gas to be detected from entering the chamber module 1 and polluting the chamber module 1 or affecting the accuracy of the detection.

Figure 3:
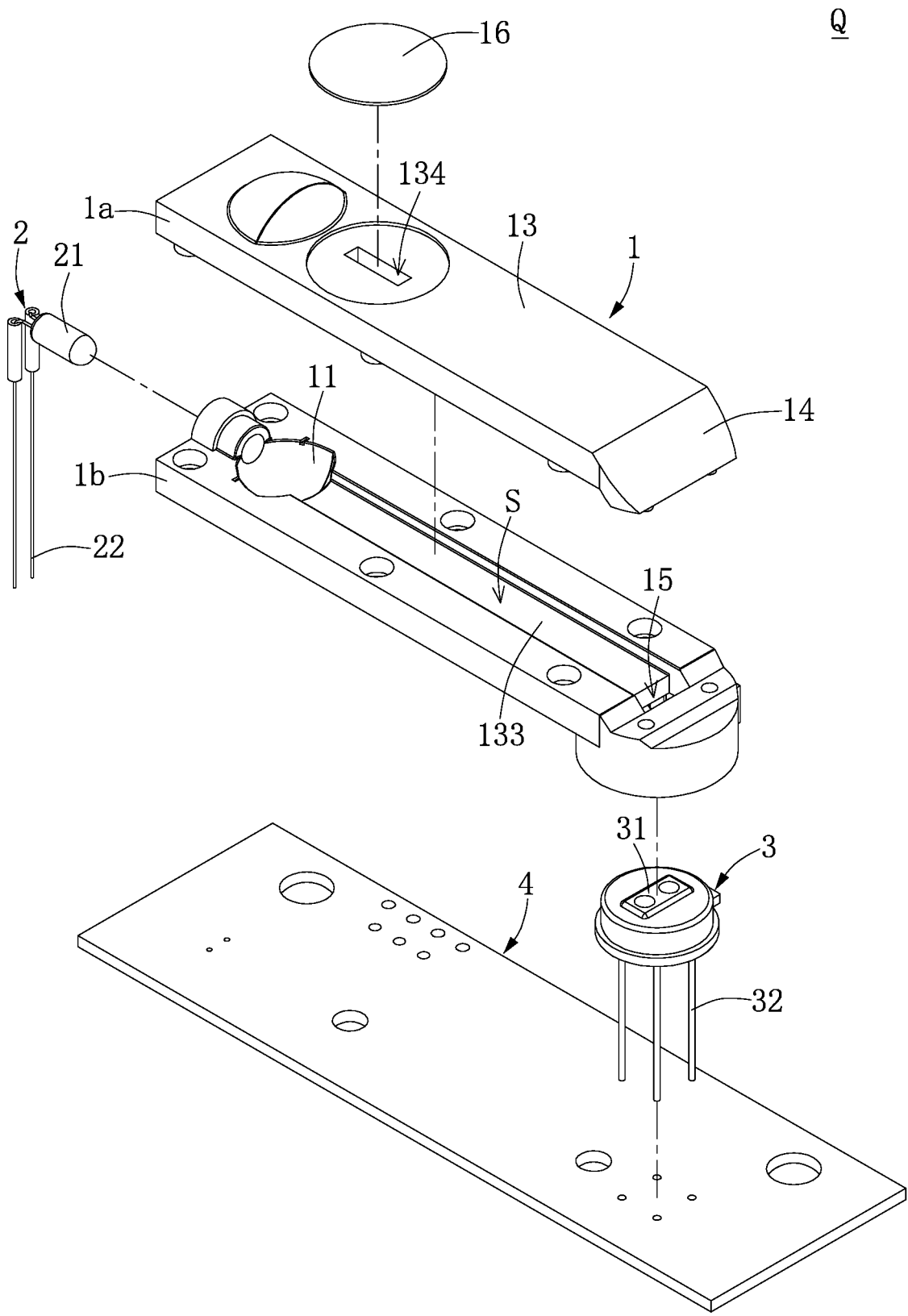
FIG. 3 is an exploded assembly schematic view of the gas detection device according to the first embodiment of the instant disclosure.
Figure 4:
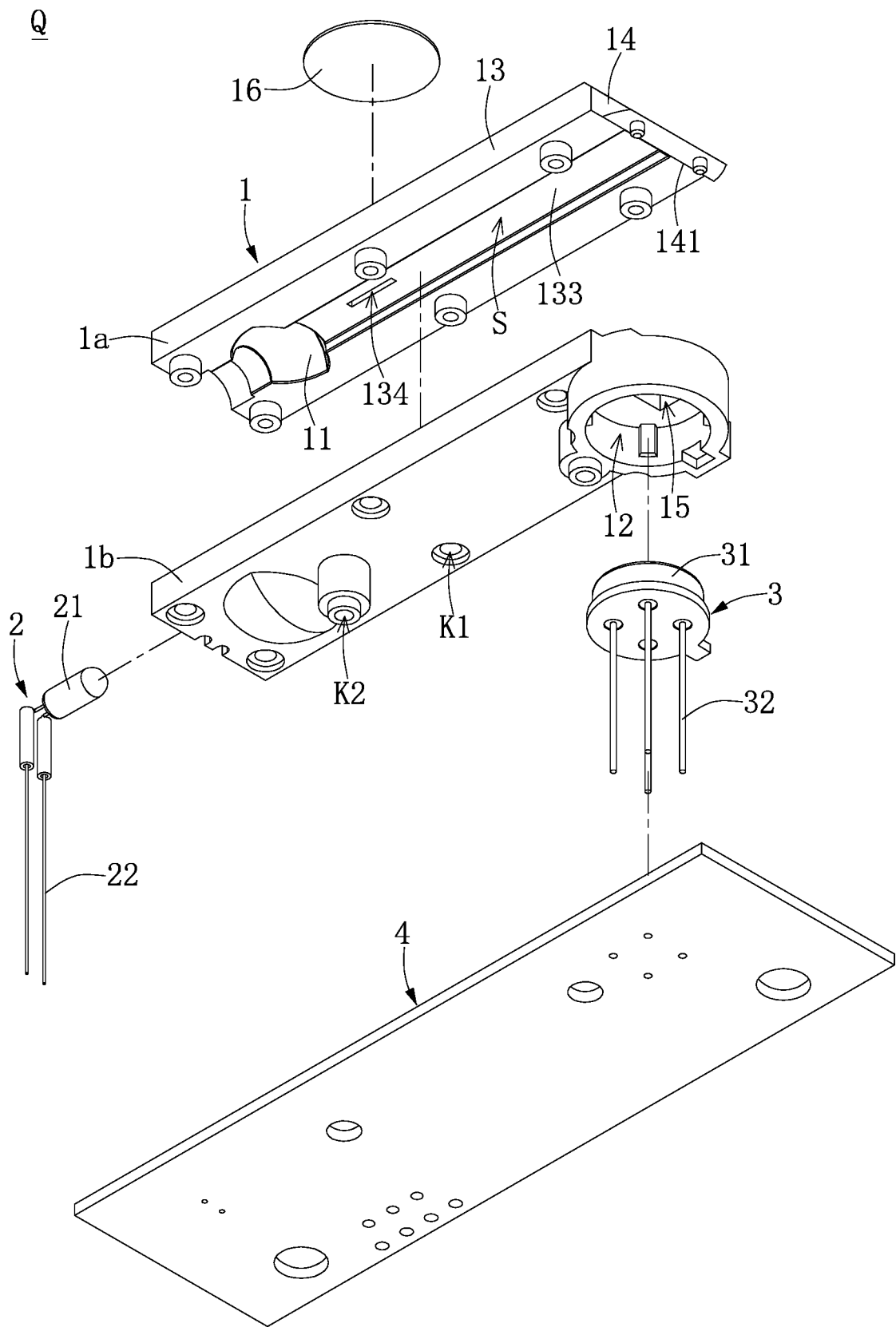
FIG. 4 is another exploded assembly schematic view of the gas detection device according to the first embodiment of the instant disclosure.

Reference is made to FIG. 1, FIG. 3 and FIG. 5. In the first embodiment of the instant disclosure, the chamber module 1 further includes a light-guiding portion 14 disposed between the sampling chamber 13 and the receiving chamber 12. The light-guiding portion 14 can have a light-guiding surface 141 for reflecting the light beam T generated by the light emitting unit 21 to the optical sensing unit 31. For example, a reflecting layer mentioned above (not shown in the figures) can be coated on the light-guiding surface 141. In another embodiment, the light-guiding surface 141 is a reflective mirror. In addition, the chamber module 1 can further include an open slot 15 which is connected between the light-guiding portion 14 and the receiving chamber 12. Therefore, a predetermined height H is present between the second surface 1332 of the sampling chamber 13 and the optical sensing unit 31. The light beam T can be projected onto the optical sensing unit 31 from the light emitting unit 21 along a T-shaped path. It should be noted that in other embodiments (for example, the embodiments shown in FIG. 12 to FIG. 14), the light-guiding portion 14 can be omitted to allow the light beam T generated by the light emitting unit 21 to be directly projected onto the optical sensing unit 31 after being repeatedly reflected by the first surface 1331 and the second surface 1332.

Figure 7:
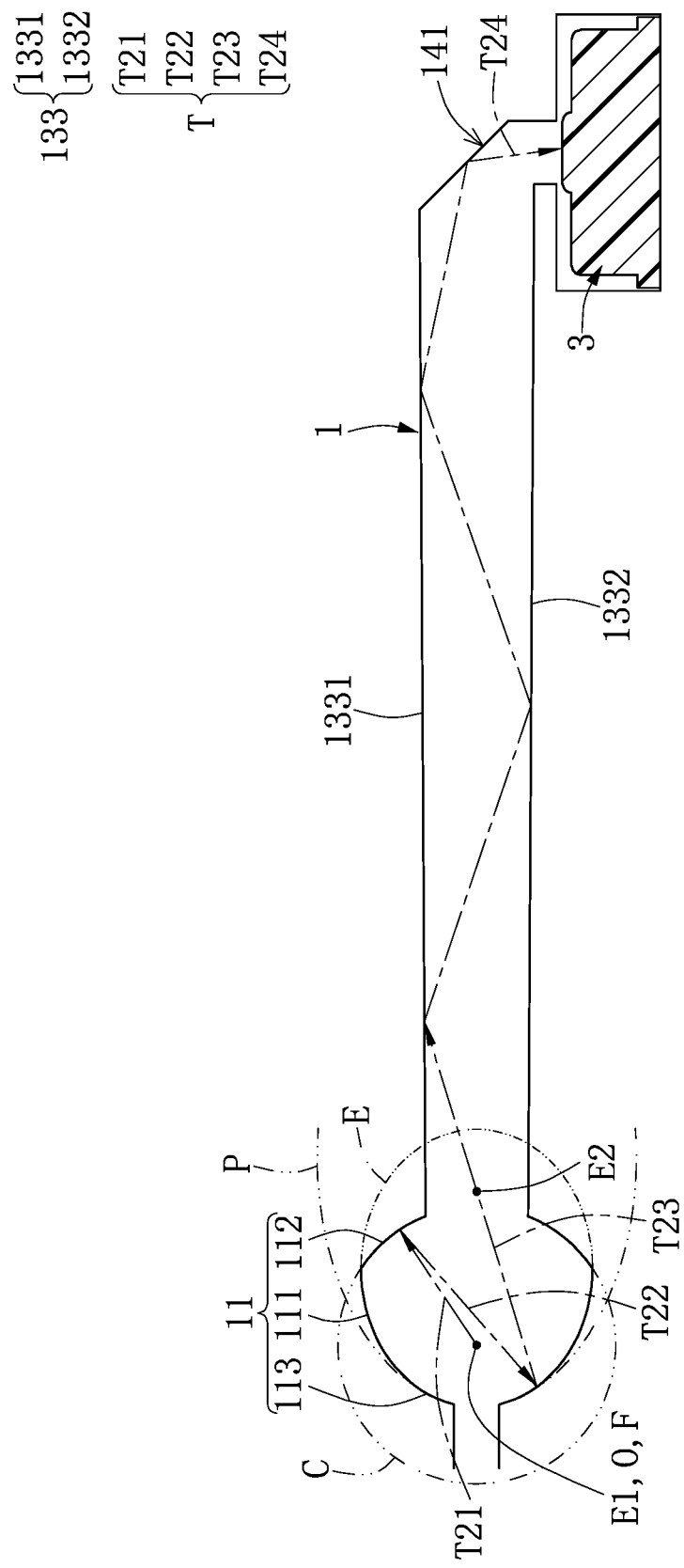
FIG. 7 depicts a path of a projection of light generated by a second reflecting structure of the gas detection device according to the first embodiment of the instant disclosure.
Figure 8:
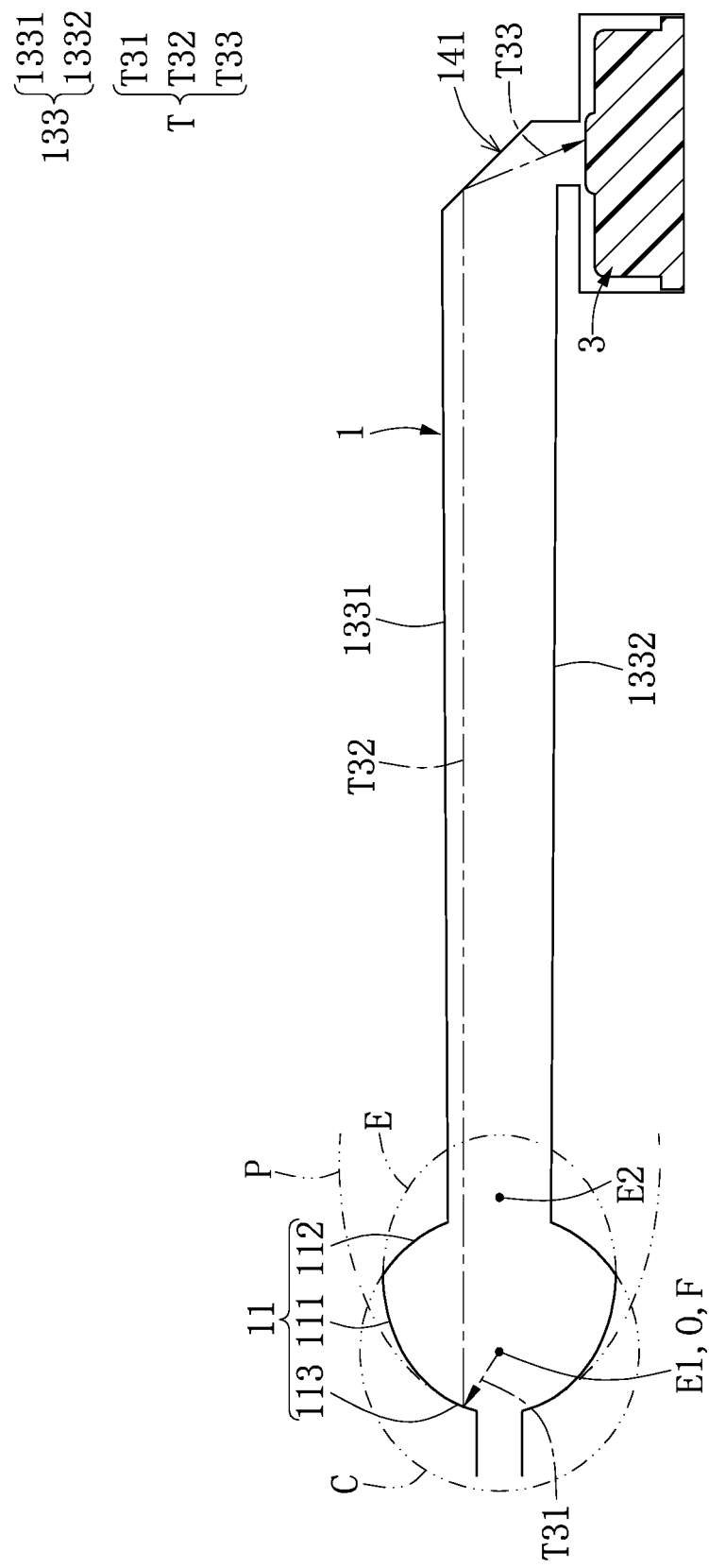
FIG. 8 depicts a path of a projection of light generated by a third reflecting structure of the gas detection device according to the first embodiment of the instant disclosure.

Reference is made to FIG. 6 to FIG. 8. The projection path of the light beam T generated by the light emitting unit 21 in the chamber module 1 is described herein. Specifically, the condensing chamber 11 can have a first reflecting structure 111, a second reflecting structure 112 connected to the first reflecting structure 111, and a third reflecting structure 113 connected to the first reflecting structure 111. The first reflecting structure 111 can be disposed between the second reflecting structure 112 and the third reflecting structure 113. For example, the curvatures of the first reflecting structure 111, the second reflecting structure 112 and the third reflecting structure 113 are different. In the embodiments of the instant disclosure, the first reflecting structure 111 can have an elliptical curved surface E, the second reflecting structure 112 can have a circular curved surface C, and the third reflecting structure 113 can have a parabolic curved surface P. Therefore, the first reflecting structure 111 has a first focus point E1 and a second focus point E2 corresponding to the first focus point E1. The second reflecting structure 112 has a central point O, and the third reflecting structure 113 has a focus point F. The first focus point E1 of the first reflecting structure 111, the central point O of the second reflecting structure 112 and the focus point F of the third reflecting structure 113 can be disposed corresponding to each other. For example, the first focus point E1, the central point O and the focus point F can overlap with each other. However, the instant disclosure is not limited thereto. In other embodiments, the first focus point E1, the central point O and the focus point F can be disposed adjacent to each other. In addition, the light emitting unit 21 can correspond to the first focus point E1, the central point O and the focus point F. Preferably, the light emitting unit 21 can be disposed directly on the first focus point E1, the central point O and the focus point F.

As shown in FIG. 6 to FIG. 8, a light beam T generated by the light emitting module 2 includes a first projecting light beam T11 projected onto the first reflecting structure 111, a second projecting light beam T21 projected onto the second reflecting structure 112 and a third projecting light beam T31 projected onto the third reflecting structure 113. The first projecting light beam T11, the second projecting light beam T21 and the third projecting light beam T31 generated by the light emitting unit 21 can be reflected by the first reflecting structure 111, the second reflecting structure 112, the third reflecting structure 113 and the inner surface 133 of the sampling chamber 13 for forming the first receiving light beam T13, the second receiving light beam T24 and the third receiving light beam T33 received by the optical sensing module 3.

As shown in FIG. 6, the light path related to the first reflecting structure 111 is described herein. Specifically, the first projecting light beam T11 can be reflected by the first reflecting structure 111 for forming a first reflecting light beam T12 projected onto the second focus point E2. Therefore, the first reflecting light beam T12 can cooperate with the inner surface 133 in the sampling chamber 13 for forming a first receiving light beam T13 projected onto the optical sensing unit 31 and received by the optical sensing unit 31. For example, in the embodiments of the instant disclosure, the sampling chamber 13 can be a rectangular chamber and have the first surface 1331, the second surface 1332, the third surface and the fourth surface. However, in other implementations, the cross section of the sampling chamber 13 can have the shape of a pentagon, a hexagon or a polygon. In other words, the first reflecting light beam T12 can be repeatedly reflected by the surfaces in the sampling chamber 13 for forming the first receiving light beam T13 projected onto the optical sensing unit 31. In the first embodiment of the instant disclosure, the first reflecting light beam T12 can be reflected by the inner surfaces of the sampling chamber 13 and the light-guiding surface 141 of the light-guiding portion 14 for forming the first receiving light beam T13 of the optical sensing unit 31.

As shown in FIG. 7, the light path related to the second reflecting structure 112 is described herein. Specifically, the second projecting light beam T21 is reflected by the second reflecting structure 112 for forming the second reflecting light beam T22 projected onto the first reflecting structure 111. The second reflecting light beam T22 is reflected by the first reflecting structure 111 for forming the second projecting light beam T21 projected onto the second focus point E2. The third reflecting light beam T23 and the inner surfaces of the sampling chamber 13 cooperate with each other for forming the second projecting light beam T21 projected onto the optical sensing unit 31 and received by the optical sensing unit 31. In other words, the third reflecting light beam T23 can be repeatedly reflected by the inner surface 133 of the sampling chamber 13 for forming the second projecting light beam T21 projected onto the optical sensing unit 31. In the first embodiment of the instant disclosure, the third reflecting light beam T23 can be reflected by the inner surface 133 of the sampling chamber 13 and the light-guiding surface 141 of the light-guiding portion 14 for forming the second projecting light beam T21 projected onto the optical sensing unit 31. It should be noted that generally, the second reflecting light beam T22 can pass through the central point O of the second reflecting structure 112 and the first focus point E1 of the first reflecting structure 111. However, in order to avoid any confusion, the second reflecting light beam T22 in FIG. 7 is shown without passing through the first focus point E1.

As shown in FIG. 8, the light path related to the third reflecting structure 113 is described herein. Specifically, the third projecting light beam T31 is reflected by the third reflecting structure 113 for forming the third receiving light beam T33 projected onto the optical sensing unit 31 and received by the optical sensing unit 31. In the first embodiment of the instant disclosure, the third projecting light T31 is reflected by the third reflecting structure 113 and forms a fourth reflecting light beam T32, and the fourth reflecting light beam T32 can be reflected by the light-guiding surface 141 of the light-guiding portion 14 for forming the third receiving light beam T33 projected onto the optical sensing unit 31.

Further referring to FIG. 5, specifically, in the first embodiment of the instant disclosure, the light guiding portion 14 can be connected between the second opening 132 and the receiving chamber 12. The light-guiding surface 141 of the light-guiding portion 14 can incline for a predetermined angle θ ranging from 30 to 60 degrees relative to a horizontal axis HH. In another embodiment, the light-guiding surface 141 of the light-guiding portion 14 inclines at a predetermined angle θ ranging from 30 to 60 degrees relative to the second surface 1332 of the first surface 1331. In other words, the first surface 1331 or the second surface 1332 of the optical sensing unit 31 can be parallel to the horizontal axis HH. Preferably, the predetermined angle θ is 45 degrees. In addition, the open slot 15 can preferably be connected between the light-guiding portion 14 and the receiving chamber 12. In FIG. 5, the open slot 15 has a predetermined width W, and the second surface 1332 of the second opening 132 and the optical sensing unit 31 have a predetermined height H therebetween. The predetermined width W and the predetermined height H comply with the following equation: $(0.8*W) \leq H \leq (3*W)$, in which H is the predetermined height H and W is the predetermined width W.

Reference is made to FIG. 5 and FIG. 9 to FIG. 11. The first surface 1331 and the second surface 1332 adjacent to the first opening 131 can have a first predetermined distance L1 therebetween, the first surface 1331 and the second surface 1332 adjacent to the second opening 132 can have a second predetermined distance L2 therebetween. In the embodiments of the instant disclosure, in order to change the projecting angles of the first reflecting light beam T12 or the third reflecting light beam T23 on the optical sensing unit 31, the first predetermined distance L1 and the second predetermined distance L2 can be different. Preferably, the second predetermined distance L2 is larger than the first predetermined distance L1. Therefore, the cross section of the first opening 131 is smaller than that of the second opening 132. In addition, the predetermined height H and the second predetermined distance L2 can comply with the following equation: $(0.8*L2) \leq H \leq (3*L2)$, in which H is the predetermined height H and L2 is the second predetermined distance L2. In other words, the predetermined width W can be equal to the second predetermined distance L2.

In addition, for example, in the first embodiment of the instant disclosure, the cross section of the rectangular sampling chamber 13 is preferably larger than or equal to the sensing area of the optical sensing unit 31. In addition, since the existing double channel infrared sensor has a size of about 4 millimeter (mm)×2 mm, the second predetermined distance L2 can be 2.1 mm and the predetermined width W can be equal to the second predetermined distance L2. However, the instant disclosure is not limited thereto. In other implementations, the predetermined width W can range from $(1.1*L2)$ to $(2.3*L2)$. The predetermined height H can range from 1 mm to 2 mm. Preferably, the predetermined height H is 1.5 mm. However, the instant disclosure is not limited thereto.

Figure 9:
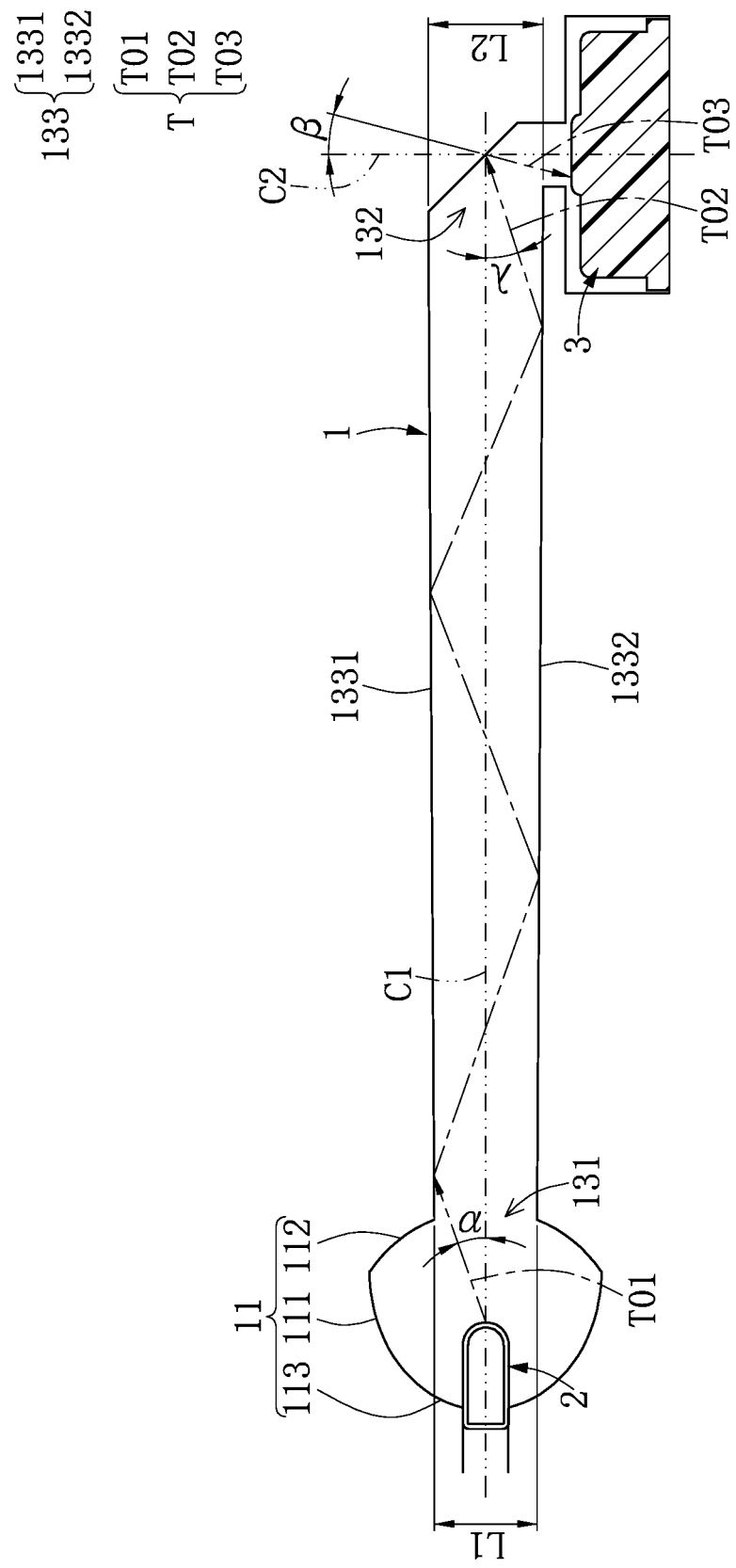
FIG. 9 depicts a path of projection of a light beam in the gas detection device according to the first embodiment of the instant disclosure.
Figure 10:
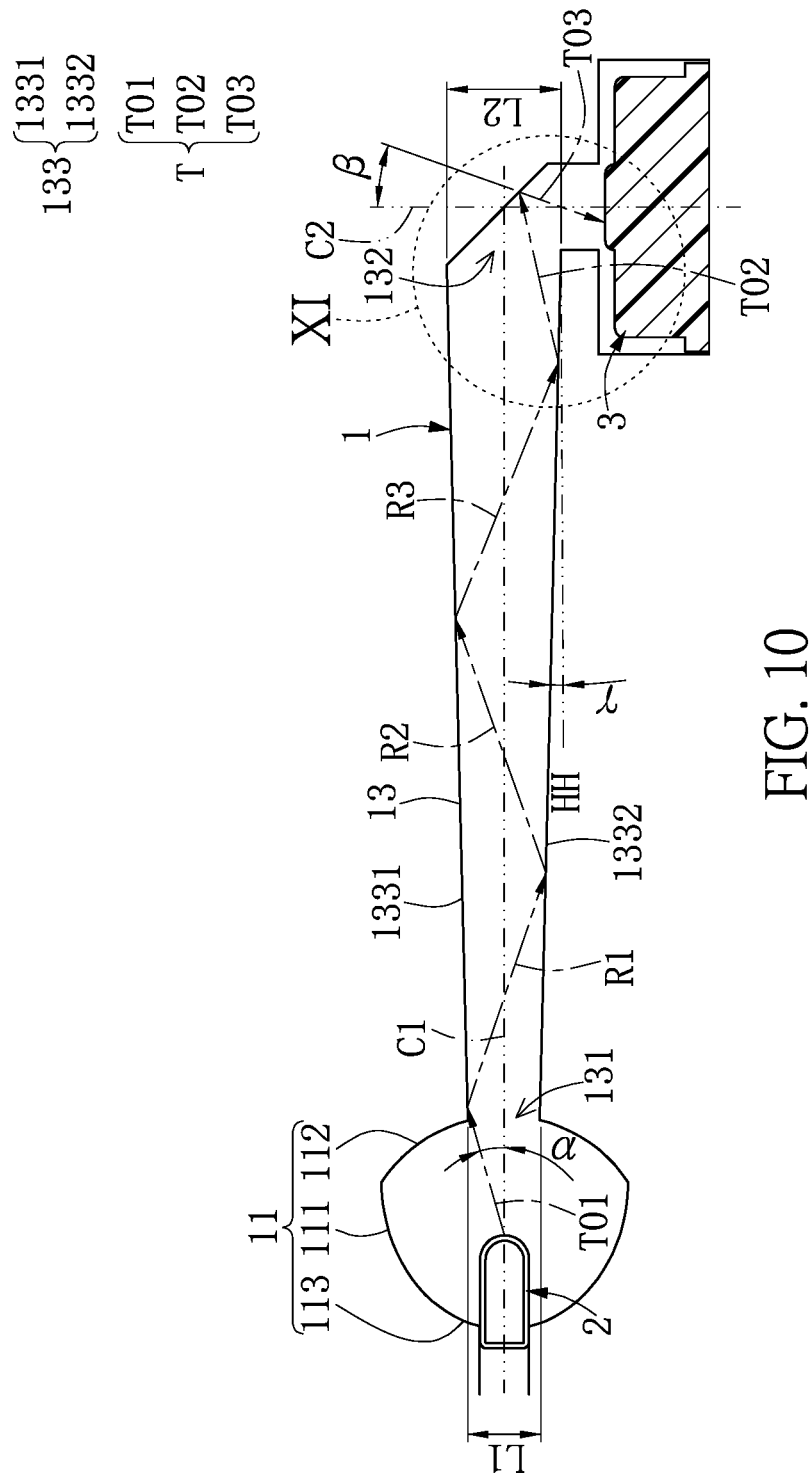
FIG. 10 depicts another path of projection of a light beam in the gas detection device according to the first embodiment of the instant disclosure.
Figure 11:
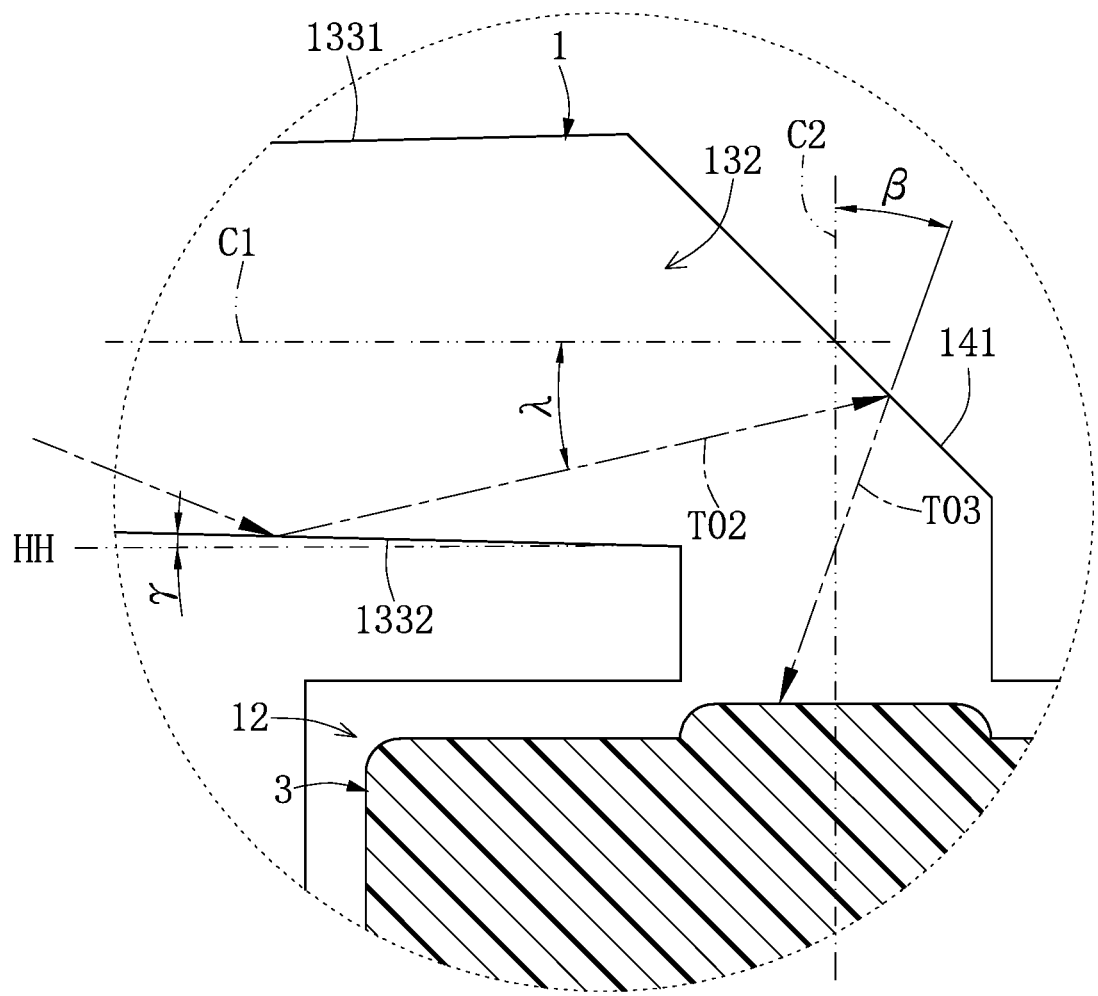
FIG. 11 is a fragmentary enlarged view of part XI in FIG. 10.

Reference is made to FIG. 9 to FIG. 11. FIG. 9 depicts an implementation in which the first surface 1331 and the second surface 1332 are parallel to each other, i.e., the second predetermined distance L2 is equal to the first predetermined distance L1 and the cross section of the first opening 131 is equal to that of the second opening 132. FIG. 10 depicts an implementation in which the first surface 1331 and the second surface 1332 are not parallel to each other, i.e., the first predetermined distance L1 and the second predetermined distance L2 are different or the cross section of the first opening 131 is smaller than that of the second opening 132. The difference between the light paths resulted from each of the arrangements of the first opening 131 and the second opening 132 are described below.

Specifically, as shown in FIG. 9, the light emitting module 2 can have a first central axis C1. The first central axis C1 can pass through the light source center (not shown) of the light emitting unit 21. The optical sensing module 3 can have a second central axis C2. The second central axis C2 can pass through the central point O for receiving light of the optical sensing module 3. In the first embodiment of the instant disclosure, the first central axis C1 and the second central axis C2 are perpendicular to each other. However, the instant disclosure is not limited thereto.

In FIG. 9, the predetermined angle θ of the light-guiding surface 141 is 45 degrees. In addition, the description herein only discusses the difference between the implementation in which the cross section of the first opening 131 is equal to that of the second opening 132 and the implementation in which the cross section of the first opening 131 is smaller than that of the second opening 132, and the first projecting light beam T11, the second projecting light beam T21 and the third projecting light beam T31 are not described herein. However, based on the selection of the cross sections, the light paths of the first receiving light beam T13, the second receiving light beam T24 and the third receiving light beam T33 can be changed as well.

As shown in FIG. 9, the light beam T can include a projecting light beam T01 projected onto the first surface 1331. The projecting light beam T01 is reflected by the first surface 1331 and the second surface 1332 for forming an incident light beam T02 projected onto the light-guiding surface 141. The incident light beam T02 is reflected by the light-guiding surface 141 for forming a receiving light beam T03 projected onto the optical sensing module 3 and received by the optical sensing module 3. The projecting light beam T01 and the first central axis C1 have a projecting angle α therebetween, the incident light beam T02 and the second central axis C2 have a receiving angle β therebetween, and the incident light beam T02 and the first central axis C1 have an incident angle λ, therebetween. In the implementation shown in FIG. 9, the projecting angle α between the projecting light beam T01 and the first central axis C1 is equal to the incident angle λ, between the incident light beam T02 and the first central axis C1. Next, the incident light beam T02 is reflected by the light-guiding surface 141 of 45 degrees for forming the receiving light beam T03 projected onto the optical sensing module 3 and received by the optical sensing module 3. Since the first surface 1331 and the second surface 1332 are parallel to each other and the light-guiding surface 141 is 45 degrees, the incident angle λ, and the projecting angle α are equal, and the receiving angle β is equal to the projecting angle α.

Reference is made to FIG. 10 and FIG. 11. In the following embodiment, the first predetermined distance L1 and the second predetermined distance L2 are different, and the second predetermined distance L2 is larger than the first predetermined distance L1. In other words, the first surface 1331 and the second surface 1332 are not parallel to each other. In the present embodiment, the projecting light beam T01 reflects between the first surface 1331 and the second surface 1332 for N times. An inclined angle γ is presented between the first surface 1331 and the horizontal axis HH, and between the second surface 1332 and the horizontal axis HH. In addition, the projecting light beam T01 can be reflected by the first surface 1331 and the second surface 1332 for forming M reflecting light beams reflecting between the first surface 1331 and the second surface 1332 (for example, the first reflecting light beam R1, the second reflecting light beam R2, and the third reflecting light beam R3). The $M^{th}$ reflecting light beam and the first central axis C1 have an included angle smaller than an included angle between the $(M-1)^{th}$ reflecting light beam and the first central axis C1. In other words, since the first surface 1331 and the second surface 1332 both have an inclined angle γ relative to the first central axis C1, the reflecting angle of the latter reflection is smaller than that of the previous reflection. Therefore, compared to the situation in which the first predetermined distance L1 and the second predetermined distance L2 are equal, in the situation that the second predetermined distance L2 is larger than the first predetermined distance L1, the optical sensing module 3 can receive more infrared light.

For example, as shown in FIG. 10 and FIG. 11, the predetermined angle θ of the first opening 131 is 45 degrees, the inclined angle γ is 0.5 degrees, and the projecting angle α is 20 degrees. Specifically, the light beam T includes a projecting light beam T01 projected onto the first surface 1331, and the projecting light beam T01 is reflected by the first surface 1331 and the second surface 1332 for forming an incident light beam T02 projected onto the light-guiding surface 141. The incident light beam T02 is reflected by the light-guiding surface 141 for forming a receiving light beam T03 projected onto the optical sensing module 3 and received by the optical sensing module 3. Therefore, after reflecting by the first surface 1331 and the second surface 1332, the incident light beam T02 and the first central axis C1 can have an incident angle γ, of 16 degrees. The incident light beam T02 having the incident angle γ, of 16 degrees is reflected by the light-guiding surface 141 of 45 degrees and forms a receiving light beam T03 having a receiving angle β of 16 degrees. In addition, it should be noted that the projecting angle is not limited to 20 degrees. In other embodiments, different optical sensing units 31 can each have more preferable incident angle other than 20 degrees. The calculation of the angles is described later.

Second Embodiment

Figure 12:
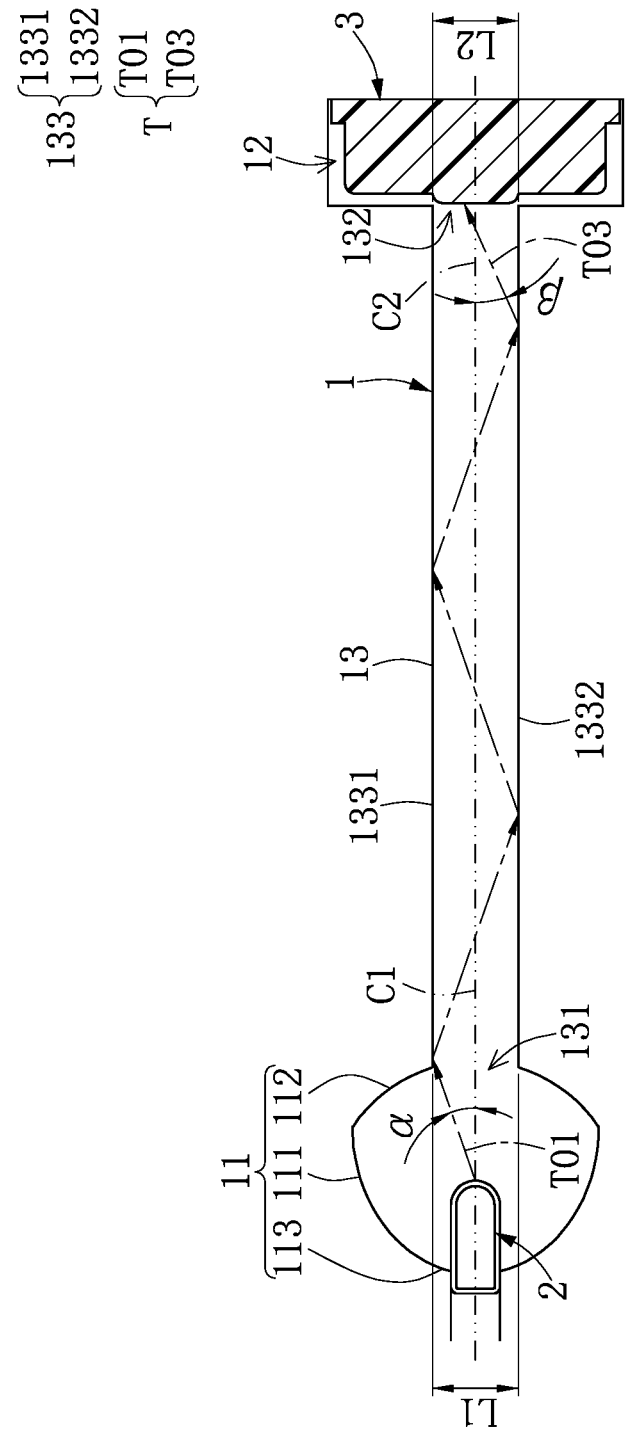
FIG. 12 depicts a path of projection of a light beam in the gas detection device according to a second embodiment of the instant disclosure.
Figure 13:
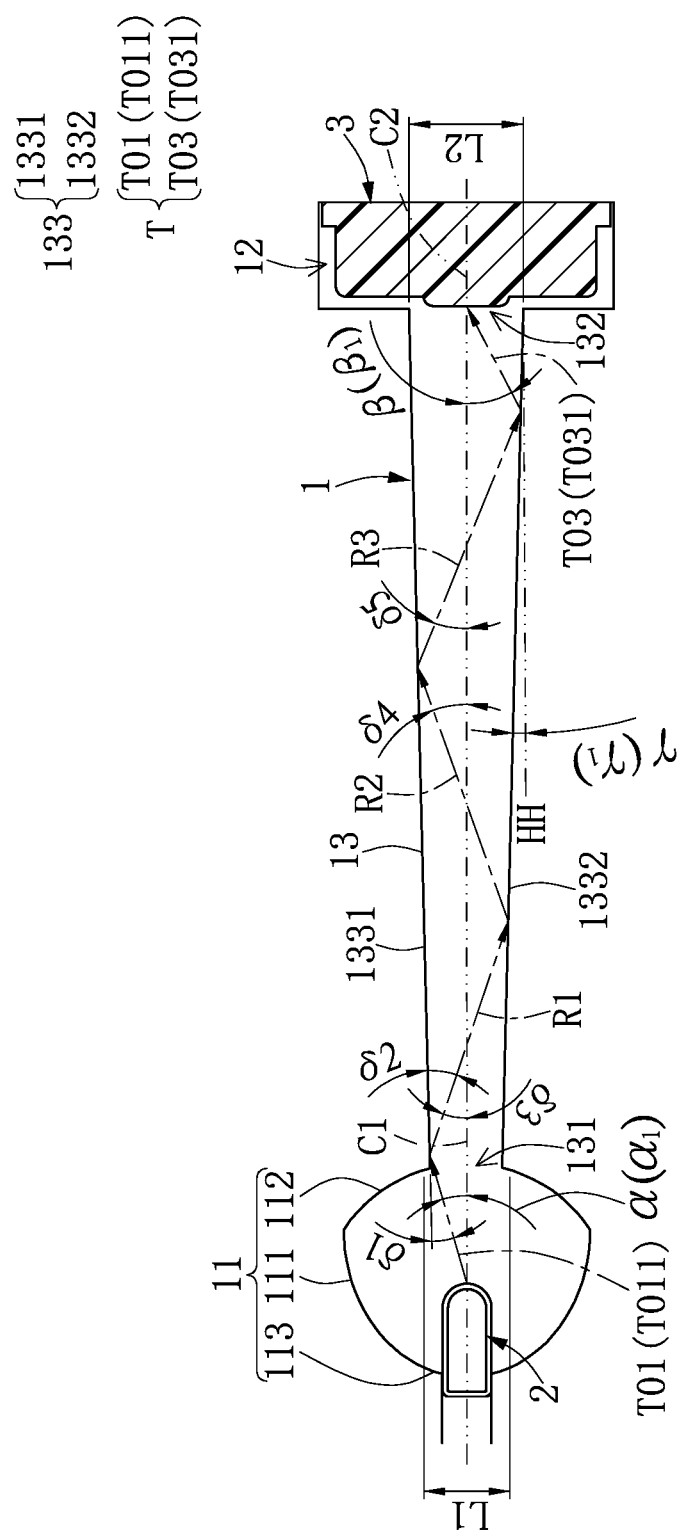
FIG. 13 depicts another path of projection of a light beam in the gas detection device of according to a second embodiment of the instant disclosure.

Reference is made to FIG. 12 and FIG. 13. Comparing FIG. 12 to FIG. 9, the main difference between the second embodiment and the first embodiment is that the chamber module 1 provided by the second embodiment does not include the light-guiding portion 14 and the open slot 15. The light beam T generated by the light emitting unit 21 is directly projected onto the optical sensing unit 31. In other words, the light emitting module 2 can have a first central axis C1 passing through the light source center (not shown) of the light emitting unit 21. The optical sensing module 3 can have a second central axis C2 passing through the center of the optical sensing module 3 for receiving light beams. It should be noted that in the second embodiment of the instant disclosure, the first central axis C1 and the second central axis C2 are parallel and coaxial. However, the instant disclosure is not limited thereto. In addition, other structural features of the gas detection device Q provided by the second embodiment are similar to those of the previous embodiment, and the details thereof are not reiterated herein.

In addition, FIG. 12 shows the implementation in which the first surface 1331 and the second surface 1332 of the FIG. 12 are parallel to each other, i.e., the second predetermined distance L2 is equal to the first predetermined distance L1, and the cross section of the first opening 131 is equal to the cross section of the second opening 132. FIG. 13 shows the implementation in which the first surface 1331 and the second surface 1332 are not parallel to each other, i.e., the first predetermined distance L1 and the second predetermined distance L2 are different. The light paths in the two different embodiments are described herein.

As shown in FIG. 12, the projecting light beam T01 and the first central axis C1 have a projecting angle α therebetween, and the receiving light beam T03 and the second central axis C2 have a receiving angle β therebetween. It should be noted that since the first predetermined distance L1 and the second predetermined distance L2 are equal, i.e., the first surface 1331 and the second surface 1332 of the sampling chamber 13 are parallel to each other, based on the reflection law, when the projecting angle α is 20 degrees, the receiving angle β is 20 degrees as well.

As shown in FIG. 13, the second predetermined distance L2 adjacent to the second opening 132 of the optical sensing module 3 is larger than the first predetermined distance L1 adjacent to the first opening 131 of the light emitting module 2. Specifically, the light beam T also includes a projecting light beam T01 projected onto the first surface 1331 (or referred to as the first projecting light beam T011) and a receiving light beam T03 received by the optical sensing module 3 (or referred to as the first receiving light beam T031). The projecting light beam T01 and the first central axis C1 have a projecting angle α therebetween (or referred to as the first projecting angle α1), and the receiving light beam T03 and the second central axis C2 have a receiving angle β therebetween (or referred to the first receiving angle β1). It should be noted that in the embodiments of the instant disclosure, the first central axis C1 can be parallel to the horizontal axis HH.

As shown in FIG. 13, in the embodiments of the instant disclosure, the projecting light beam T01 reflects between the first surface 1331 and the second surface 1332 for N times. An inclined angle γ is present between the first surface 1331 and the horizontal axis HH and between the second surface 1332 and the horizontal axis HH. The receiving angle β between the receiving light beam T03 and the second central axis C2 complies with the equation: $\beta = \alpha - 2\gamma N$, wherein α is the projecting angle, β is the receiving angle, γ is the inclined angle and N is the time of reflection. It should be noted that in the embodiments of the instant disclosure, the inclined angle γ can range between 0.1 and 5 degrees, preferably, between 0.3 and 3 degrees, and most preferably, 0.5 degrees. However, the instant disclosure is not limited thereto.

In addition, the projecting light beam T01 is reflected by the first surface 1331 and the second surface 1332 and forms M reflecting light beams reflecting between the first surface 1331 and the second surface 1332 (such as the first reflecting light beam R1, the second reflecting light beam R2 and the third reflecting light beam R3). The included angle between the $M^{th}$ reflecting light beam and the first central axis C1 is smaller than the included angle between the $(M-1)^{th}$ reflecting light beam and the first central axis C1. In other words, since the first surface 1331 and the first central axis C1, and the second surface 1332 and the first central axis C1 both have an inclined angle γ therebetween, the reflecting angle of the latter reflection is smaller than that of the previous reflection.

For example, when the projecting angle α between the projecting light beam T01 and the first central axis C1 is 20 degrees, and the inclined angle γ is 0.5 degrees, the projecting light beam T01 and the first surface 1331 have a first angle δ1 of 19.5 degrees. The projecting light beam T01 is reflected by the first surface 1331 and forms a first reflecting light beam R1 projected onto the second surface 1332. Based on the reflection law, the first reflecting light beam R1 and the first surface 1331 have a second angle δ2 of 19.5 degrees, and the first reflecting light beam R1 and the first central axis C1 have a third angle δ3 of 19 degrees. The first reflecting light beam R1 is reflected by the second surface 1332 for forming a second reflecting light beam R2 projected onto the first surface 1331. The second reflecting light beam R2 and the first central axis C1 have a fourth angle δ4 of 18 degrees therebetween. The second reflecting light beam R2 is reflected by the first surface 1331 for forming the third reflecting light beam R3 projected onto the second surface 1332. The third reflecting light beam R3 and the first central axis C1 can have a fifth angle δ5 of 17 degrees therebetween. The third reflecting light beam R3 is reflected by the second surface 1332 for forming a receiving light beam T03 projected onto the optical sensing module 3 and received by the optical sensing module 3. The receiving light beam T03 and the first central axis C1 have a receiving angle β of 16 degrees therebetween.

It should be noted that in the first embodiment of the instant disclosure, the first central axis C1 and the second central axis C2 are coaxial. Therefore, the receiving light beam T03 and the second central axis C2 have a receiving angle β of 16 degrees therebetween. In addition, the projecting light beam T01 is reflected by the first surface 1331 and the second surface 1332 for four times (i.e., the number of times that the projecting light beam T01 is projected onto the first surface 1331 and the second surface 1332 is 4). In other words, based on the equation $\beta = \alpha - 2\gamma N$, the receiving angle β is 20 degrees$-(2*0.5*4)$ degrees, and hence, the receiving angle β is 16 degrees. In addition, the included angle between the second reflecting light beam R2 and the first central axis C1 is smaller than the included angle between the first reflecting light beam R1 and the first central axis C1.

It should be noted that compared to the situation in which the first predetermined distance L1 and the second predetermined distance L2 are equal, when the second predetermined distance L2 is larger than the first predetermined distance L1, the optical sensing unit 31 can receive more infrared light. In other words, in a preferred embodiment, the receiving light beam T03 enters the optical sensing unit 31 vertically. In addition, it should be noted that the projecting angle α of 20 degrees is only an example and the instant disclosure is not limited thereto. In other words, different optical sensing modules 3 can have different preferable receiving angles β. In addition, in the embodiments of the instant disclosure, the distance between the first opening 131 and the second opening 132 (i.e., the length of the sampling chamber 13) can be 35 millimeter (mm) to 50 mm. However, the instant disclosure is not limited thereto.

Figure 14:
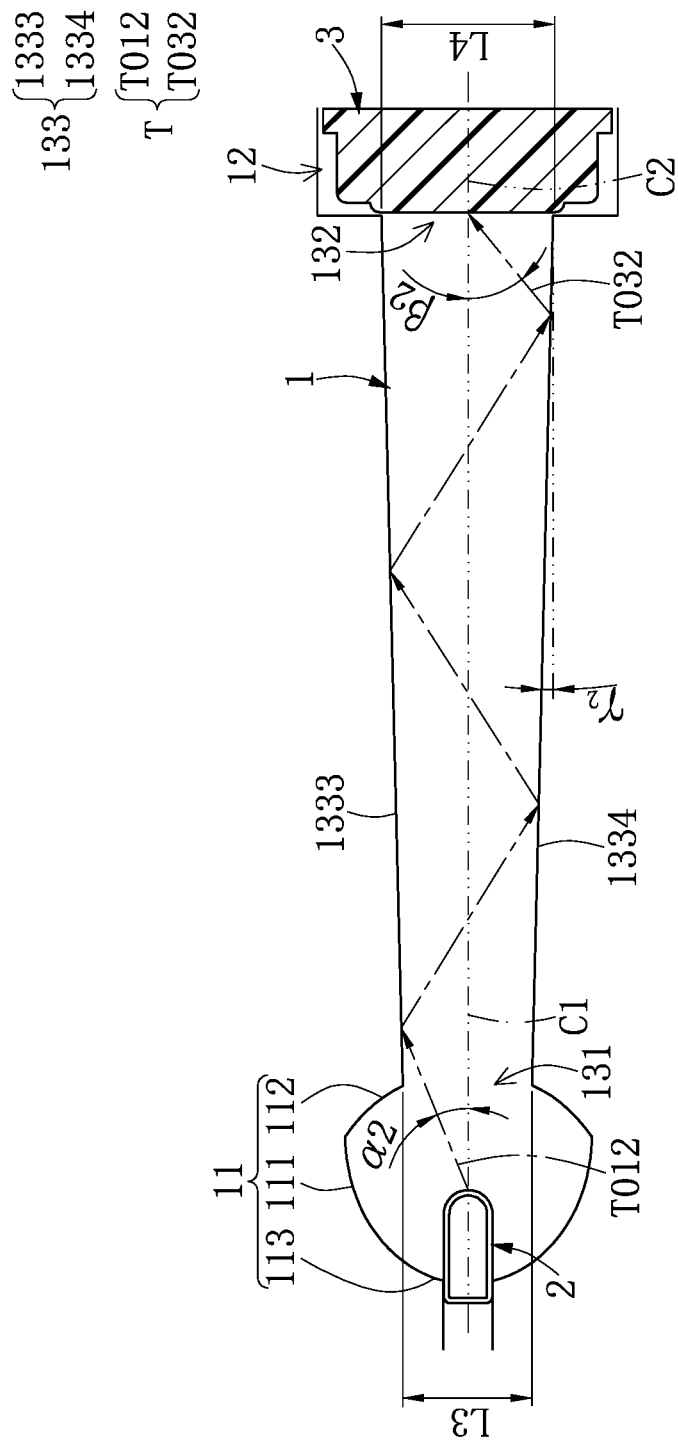
FIG. 14 depicts yet another path of projection of a light beam in the gas detection device according to the second embodiment of the instant disclosure.
Figure 15:
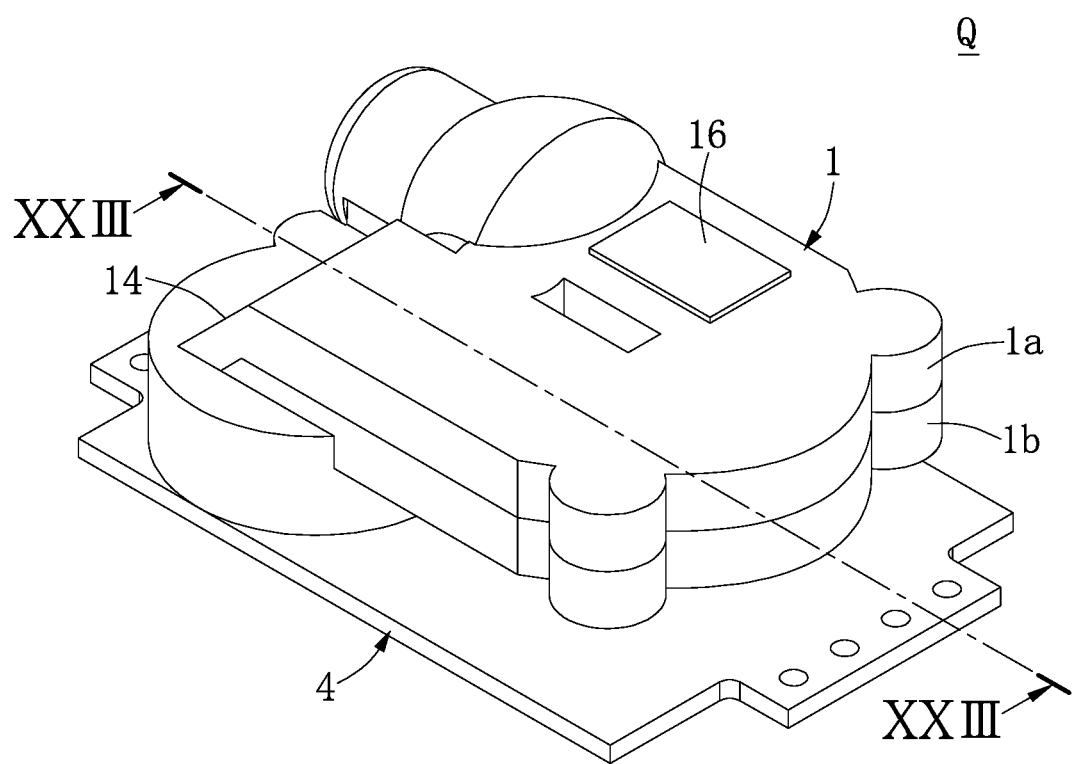
FIG. 15 is a three-dimensional assembly schematic view of a gas detection device according to the third embodiment of the instant disclosure.
Figure 16:
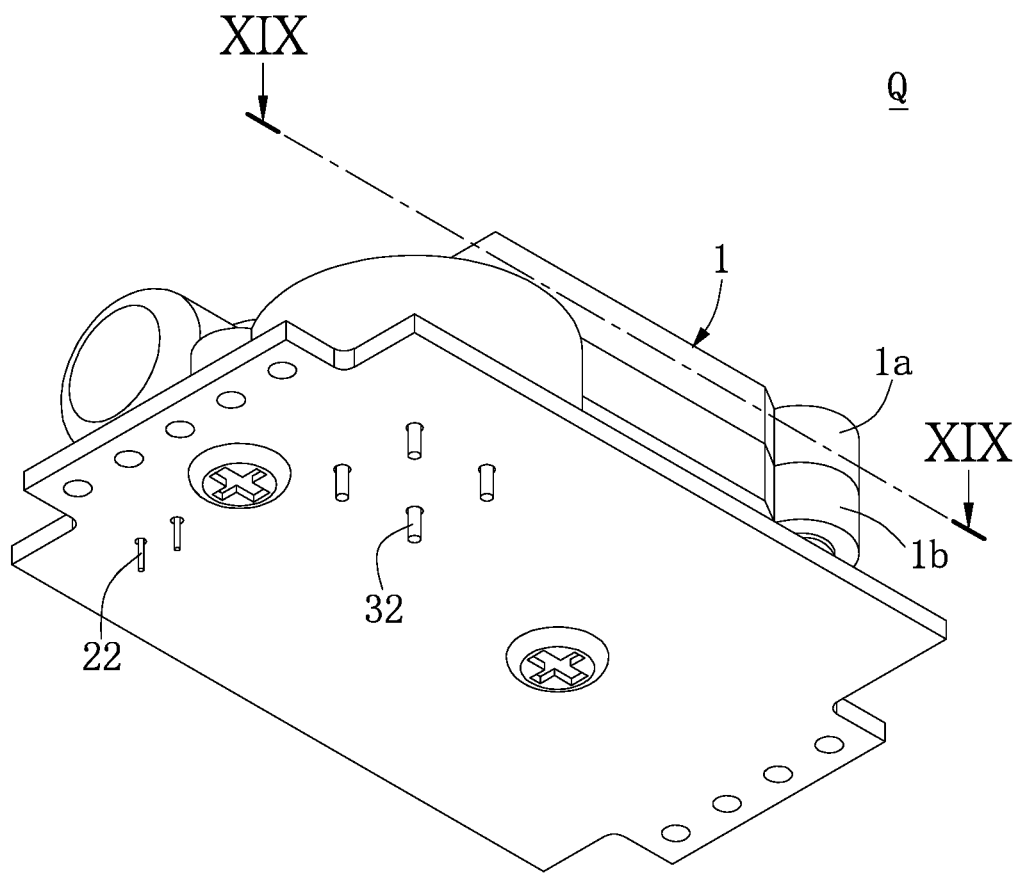
FIG. 16 is another three-dimensional assembly schematic view of a gas detection device according to a third embodiment of the instant disclosure.

Reference is made to FIG. 14. The implementation in which the third surface 1333 and the fourth surface 1334 are inclined relative to the first central axis C1 for an angle is described herein. In other words, the third surface 1333 and the fourth surface 1334 are not parallel to each other. In addition, it should be noted that the third surface 1333 and the fourth surface 1334 are respectively the left side surface and the right side surface of the sampling chamber 13. Specifically, the third surface 1333 and the fourth surface 1334 of the first opening 131 have a third predetermined distance L3 therebetween, the third surface 1333 and the fourth surface 1334 of the second opening 132 have a fourth predetermined distance L4 therebetween, and the fourth predetermined distance L4 is larger than the third predetermined distance L3.

With reference to FIG. 14 and the above description relevant to FIG. 13, the light beam T includes a first projecting light beam T011 projected onto the first surface 1331 and a second projecting light beam T012 projected onto the third surface 1333. The first projecting light beam T011 is reflected by the first surface 1331 and the second surface 1332 for forming the first receiving light beam T031 projected onto the optical sensing module 3 and received by the optical sensing module 3. The second projecting light beam T012 is reflected by the third surface 1333 and the fourth surface 1334 for forming a second receiving light beam T032 projected onto the optical sensing module 3 and received by the optical sensing module 3. The light emitting module 2 has a first central axis C1, and the first projecting light beam T011 and the first central axis C1 have a first projecting angle $\alpha_1$ therebetween. The second projecting light beam T012 and the first central axis C1 have a second projecting angle $\alpha_2$ therebetween. The optical sensing module 3 has a second central axis C2, the first receiving light beam T031 and the second central axis C2 have a first receiving angle $\beta_1$ therebetween. The second receiving light beam T032 and the second central axis C2 have a second receiving angle $\beta_2$ therebetween.

The first projecting light beam T011 reflects between the first surface 1331 and the second surface 1332 for $N_1$ times, the second projecting light beam T012 reflects between the first surface 1331 and the fourth surface 1334 for $N_2$ times, and the first central axis C1 and the second central axis C2 are parallel to the horizontal axis HH. A first inclined angle $\gamma_1$ is present between the first surface 1331 and the horizontal axis HH, and between the second surface 1332 and the horizontal axis HH. A second inclined angle $\gamma_2$ is present between the third surface 1333 and the horizontal axis HH, and between the fourth surface 1334 and the horizontal axis HH. The first receiving light beam T031 and the second central axis C2 have a first receiving angle $\beta_1$ complying with the equation: $\beta_1=\alpha_1-2\gamma_1 N_1$. The second receiving light beam T032 and the second central axis C2 have a second receiving angle $\beta_2$ complying with the equation: $\beta_2=\alpha_2-2\gamma_2 N_2$. $\alpha_1$ is the first projecting angle, $\beta_2$ is the second receiving angle, $\gamma_1$ is the first inclined angle, $\gamma_2$ is the second inclined angle, $N_1$ is the time of reflection of the first projecting light beam T011 between the first surface 1331 and the second surface 1332, and $N_2$ is the time of reflection of the second projecting light beam T012 between the third surface 1333 and the fourth surface 1334.

The reflection of the second projecting light beam T012 between the third surface 1333 and the fourth surface 1334 is similar to the first projecting light beam T011 between the first surface 1331 and the second surface 1332 and is not reiterated herein. Therefore, the second projecting angle $\alpha_2$, the second receiving angle $\beta_2$ and the second inclined angle $\gamma_2$ are similar to the first projecting angle $\alpha_1$, the first receiving angle $\beta_1$ and the first inclined angle $\gamma_1$. However, it should be noted that since the sampling space S of the sampling chamber 13 has a rectangular cross section, the third predetermined distance L3 is larger than the first predetermined distance L1, and the fourth predetermined distance L4 is larger than the second predetermined distance L2. Therefore, the second inclined angle $\gamma_2$ can be between 0.1 to 5 degrees, preferably, between 1 to 3 degrees, and more preferably, 1.5 degrees. However, the instant disclosure is not limited thereto.

In addition, as shown in FIG. 10 and FIG. 11, in the first embodiment, the light-guiding surface 141 inclines at a predetermined angle $\theta$ relative to a horizontal axis HH. The projecting light beam T1 reflects for N times between the first surface 1331 and the second surface 1332, the first central axis C1 is parallel to a horizontal axis HH. An inclined angle $\gamma$ is present between the first surface 1331 and the horizontal axis HH, and between the second surface 1332 and the horizontal axis HH. The inclined angle $\gamma$ between the incident light beam T02 and the first central axis C1 complies with the following equation: $\lambda=\alpha-2\gamma N$, in which $\alpha$ is the projecting angle, $\gamma$ is the incident angle, $\gamma$ is the inclined angle and N is the time of reflection.

Other structural features of the gas detection device provided by the second embodiment are similar to those of the previous embodiment. The implementation described in the previous embodiment can be applied to the second embodiment. Therefore, details regarding the other structural features are not reiterated herein.

Third Embodiment

Reference is made to FIG. 15 to FIG. 18. Comparing FIG. 15 with FIG. 1, the main difference between the third embodiment and the first embodiment is that the shape of the sampling chamber 13 in the gas detection device Q provided by the third embodiment is different from that of the first embodiment. In addition, in the third embodiment, the condensing chamber 11 can have only a first reflecting structure 111 and a second reflecting structure 112, and the curvature of the first reflecting structure 111 is different from that of the second reflecting structure 112. The third reflecting structure 113 is optional in the third embodiment. It should be noted that other structural features of the gas detection device Q provided by the second embodiment are similar to those of the previous embodiments and are not reiterated herein.

Referring to FIG. 19, and FIGS. 15 to 18 as supplementary illustrations, the gas detection device Q can include a chamber module 1, a light emitting module 2, an optical sensing module 3 and a substrate module 4. The chamber module 1 can include a condensing chamber 11, a receiving chamber 12 and a sampling chamber 13 connected between the condensing chamber 11 and the receiving chamber 12. In the third embodiment, the condensing chamber 11 has a first reflecting structure 111 and a second reflecting structure 112 connected to the first reflecting structure 111. However, in other implementations, a third reflecting structure 113 can be included and the instant disclosure is not limited thereto. In addition, the gas detection device Q provided by the third embodiment can include a light-guiding portion 14 having the same function as that described in the first embodiment, i.e., the light-guiding surface 141 disposed on the light-guiding portion 14 can guide the light into the optical sensing module 3.

Figure 19:
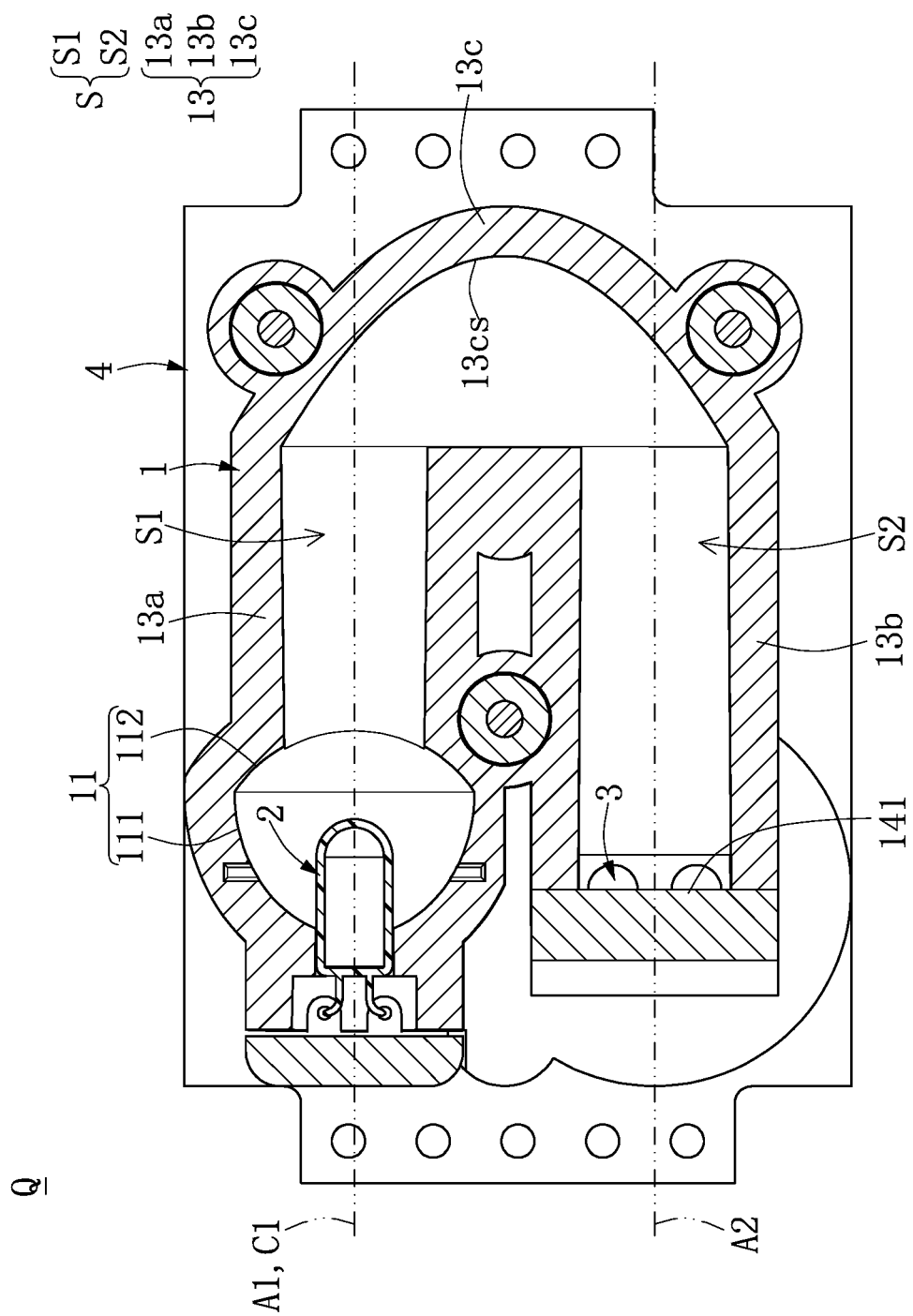
FIG. 19 is a sectional side schematic view taken along ling XIX-XIX in FIG. 15.
Figure 20:
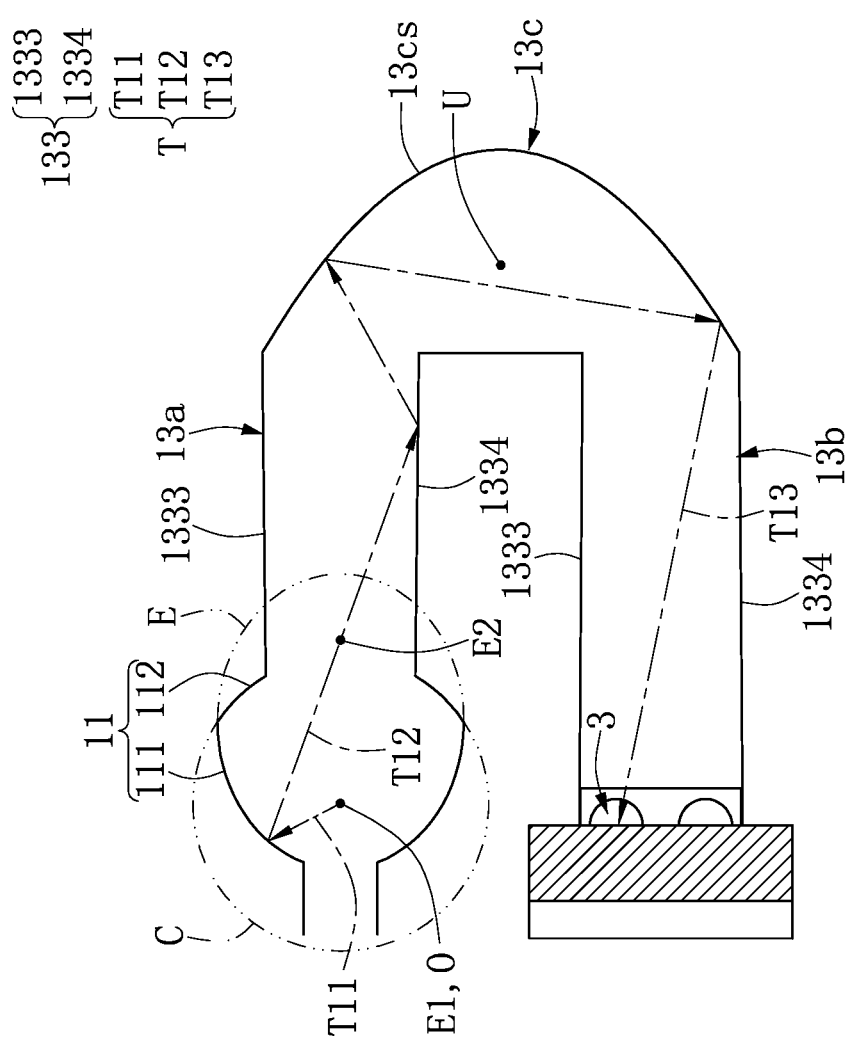
FIG. 20 depicts a path of projection of a light beam in the gas detection device according to the third embodiment of the instant disclosure.

As shown in FIG. 19 and FIG. 20, the first reflecting structure 111 has a first focus point E1, and a second focus point E2 corresponding to the first focus point E1. The second reflecting structure 112 has a central point O, and the first focus point E1 and the central point O correspond to each other. The first reflecting structure 111 has an elliptical curved surface E, and the second reflecting structure 112 has a circular curved surface C. Furthermore, the light emitting module 2 can be disposed on the condensing chamber 11 and correspond to the condensing chamber 11. The light emitting module 2 includes a light emitting unit 21, and the light emitting unit 21 can correspond to the first focus point E1 and the central point O. Preferably, the light emitting unit 21 can be disposed on the first focus point E1 and the central point O. In addition, the optical sensing module 3 includes an optical sensing unit 31 which can be disposed in the receiving chamber 12.

Figure 17:
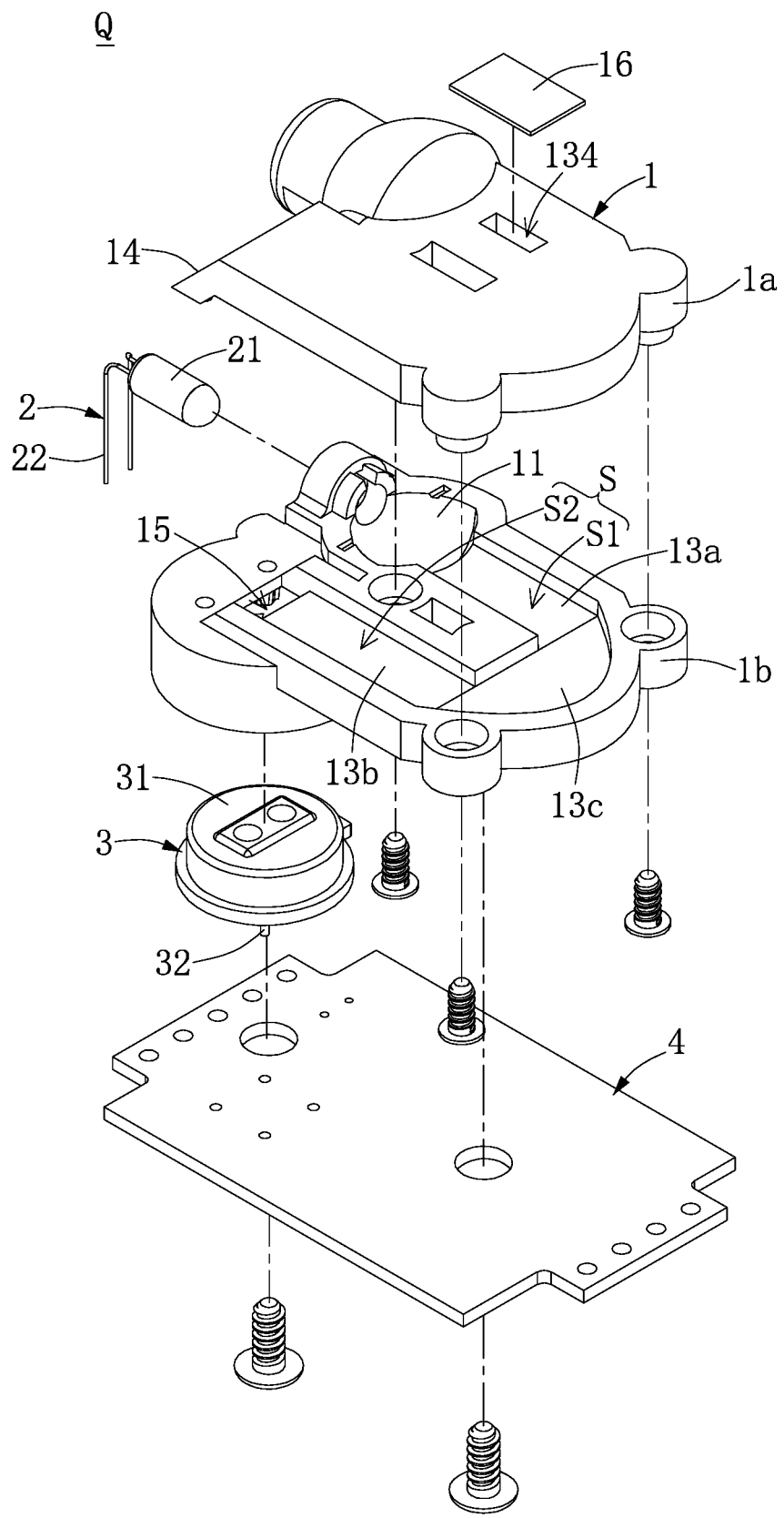
FIG. 17 is a three-dimensional exploded schematic view of a gas detection device according to the third embodiment of the instant disclosure.
Figure 18:
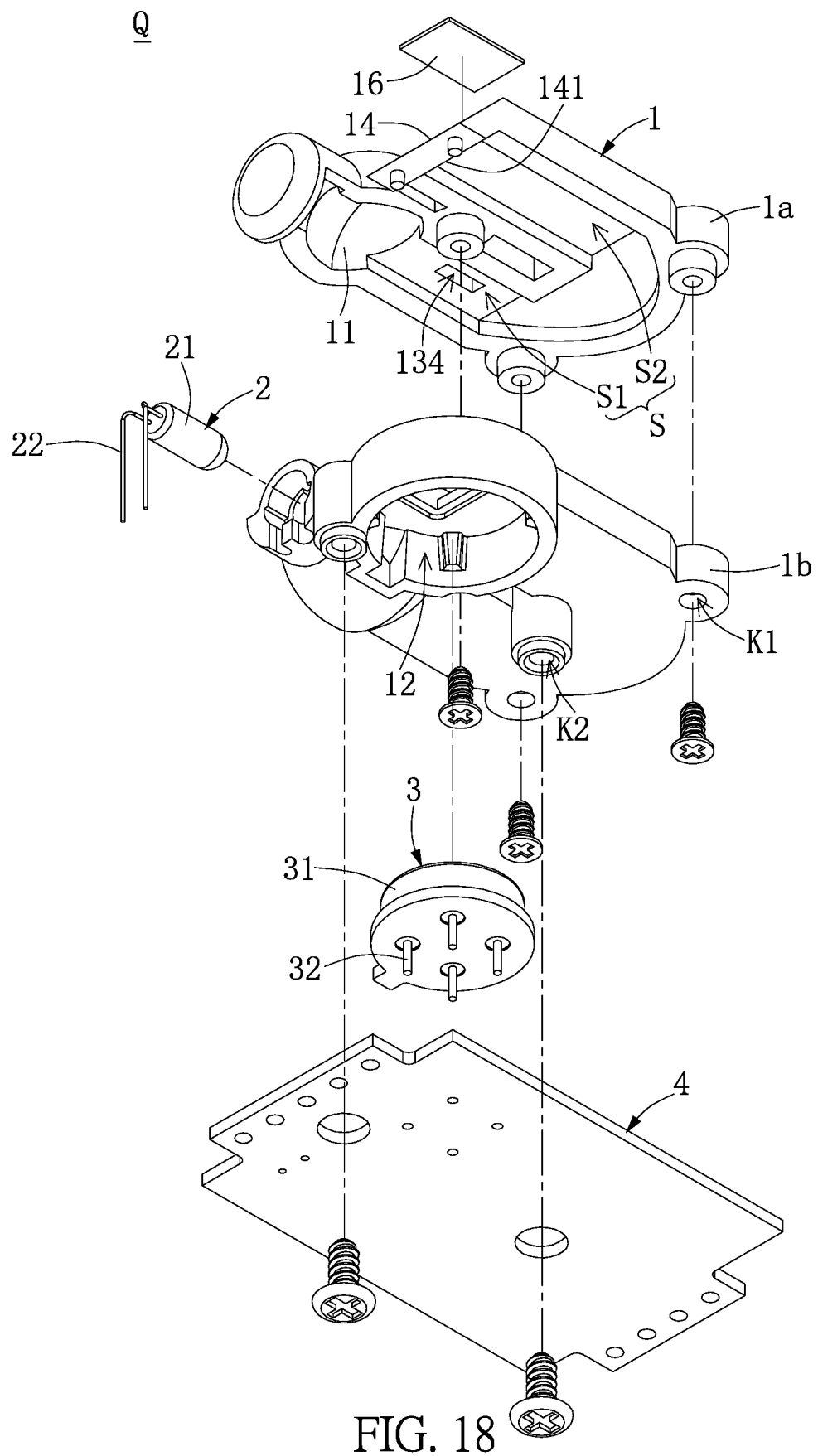
FIG. 18 is another three-dimensional exploded schematic view of a gas detection device according to the third embodiment of the instant disclosure.
Figure 32:
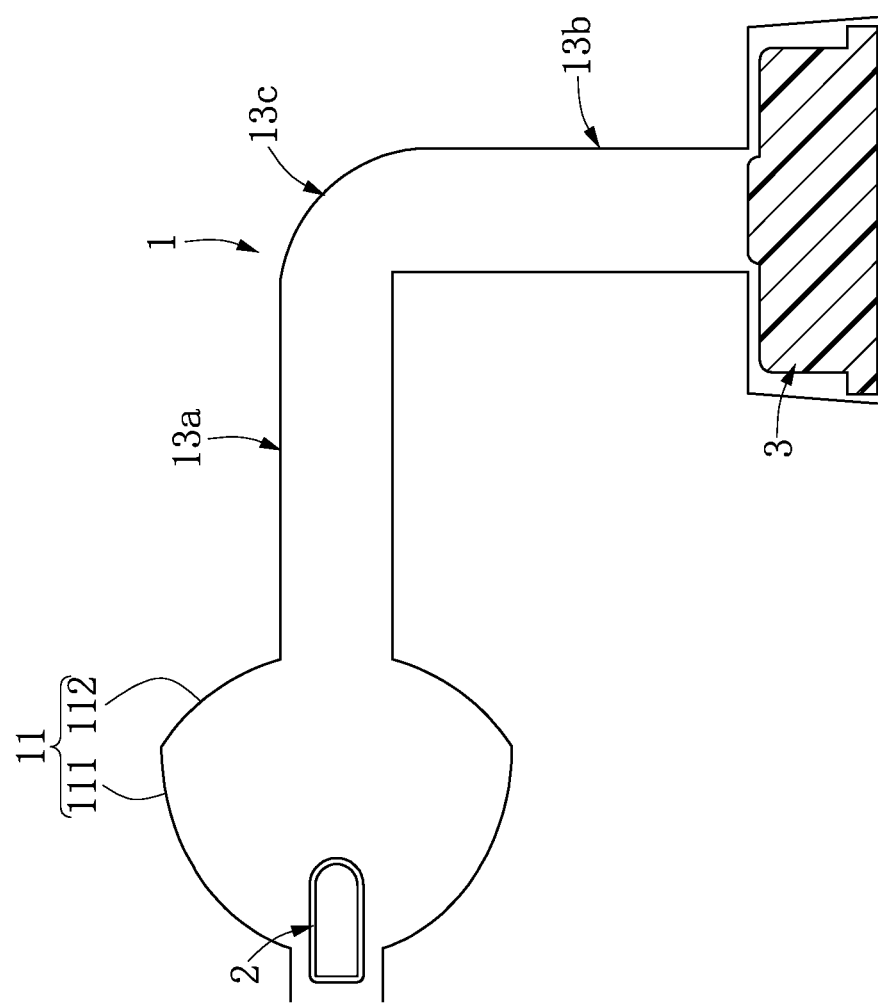
FIG. 32 is a schematic view showing the internal structure of a gas detection device of a fifth embodiment of the instant disclosure.

As shown in FIG. 17 and FIG. 19, the chamber module 1 can be formed by an upper chamber module 1a and a lower chamber module 1b. The chamber module 1 has a sampling space S (i.e., the first sampling space S1 and the second sampling space S2), and the sampling chamber 13 can include a first sampling chamber 13a connected to the condensing chamber 11, a second sampling chamber 13b connected to the receiving chamber 12 and a turning portion 13c connected between the first sampling chamber 13a and the second sampling chamber 13b. The turning portion 13c has a reflecting surface 13cs thereon. Preferably, the reflecting surface 13cs can have a parabolic curvature. In addition, the first sampling chamber 13a can have a first axis A1 and a first sampling space S1 located in the first sampling chamber 13a. The second sampling chamber 13b can have a second axis A2 and a second sampling space S2 located in the second sampling chamber 13b. The first axis A1 and the second axis A2 can be substantially parallel to each other. In the embodiments of the instant disclosure, the first sampling chamber 13a, the second sampling chamber 13b and the turning portion 13c can form a U-shape. However, the instant disclosure is not limited thereto. For example, in other embodiments, the first sampling chamber 13a, the second sampling chamber 13b and the turning portion 13c can form an L-shape (as shown in FIG. 32).

Reference is made to FIG. 20 to FIG. 23. A light beam T generated by the light emitting module 2 includes a first projecting light beam T11 projected onto the first reflecting structure 111, a second projecting light beam T21 projected onto the second reflecting structure 112 and a projecting light beam T41 projected onto the reflecting surface 13cs. The first projecting light beam T11, the second projecting light beam T21 and the projecting light beam T41 generated by the light emitting unit 21 can be reflected by the first reflecting structure 111, the second reflecting structure 112, the inner surface 133 of the sampling chamber 13 (including the first surface 1331, the second surface 1332, the third surface 1333, and the fourth surface 1334) and the reflecting surface 13cs of the turning portion 13c, and respectively form the first receiving light beam T13, the second receiving light beam T24 and the reflecting light beam T42 projected onto the optical sensing module 3.

Reference is made to FIG. 20. Specifically, the first projecting light beam T11 can be reflected by the first reflecting structure 111 for forming a first reflecting light beam T12 projected onto the second focus point E2. Therefore, the first reflecting light beam T12 cooperates with the inner surface 133 in the sampling chamber 13, and the first reflecting light beam T12 is reflected by the reflecting surface 13cs for forming a first receiving light beam T13 projected onto the optical sensing unit 31 and received by the optical sensing unit 31. In the third embodiment of the instant disclosure, the first reflecting light beam T12 can be reflected by the inner surface 133 of the sampling chamber 13, the reflecting surface 13cs of the turning portion 13c and the light-guiding surface 141 of the light-guiding portion 14 for forming the first receiving light beam T13 projected onto the optical sensing unit 31.

Figure 21:
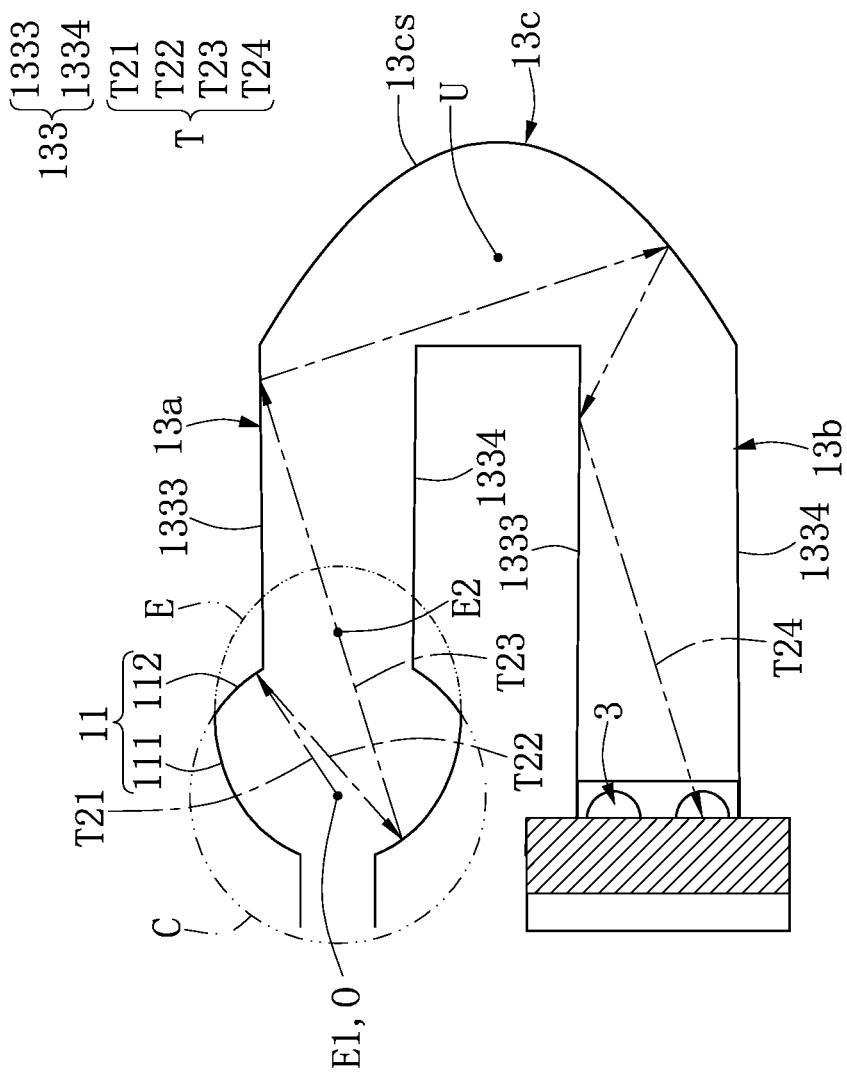
FIG. 21 depicts another path of projection of a light beam in the gas detection device according to the third embodiment of the instant disclosure.

Reference is made to FIG. 21. Specifically, the second projecting light beam T21 is reflected by the second reflecting structure 112 for forming a second reflecting light beam T22 projected onto the first reflecting structure 111. The second reflecting light beam T22 is reflected by the first reflecting structure 111 for forming a third reflecting light beam T23 projected onto the second focus point E2. The third reflecting light beam T23 cooperates with the inner surface of the sampling chamber 13, and the third reflecting light beam T23 is reflected by the reflecting surface 13cs for forming a second receiving light beam T24 projected onto the optical sensing unit 31 and received by the optical sensing unit 31. In the third embodiment of the instant disclosure, the third reflecting light beam T23 can be reflected by the inner surface 133 of the sampling chamber 13, the reflecting surface 13cs of the turning portion 13c and the light-guiding surface 141 of the light-guiding portion 14 for forming the second receiving light beam T24 projected onto the optical sensing unit 31. It should be noted that the second reflecting light beam T22 can generally pass through the central point O of the second reflecting structure 112 and the first focus point E1 of the first reflecting structure 111. However, in order to prevent any confusion, the second reflecting light beam T22 shown in FIG. 21 is depicted as not passing through the first focus point E1.

Figure 22:
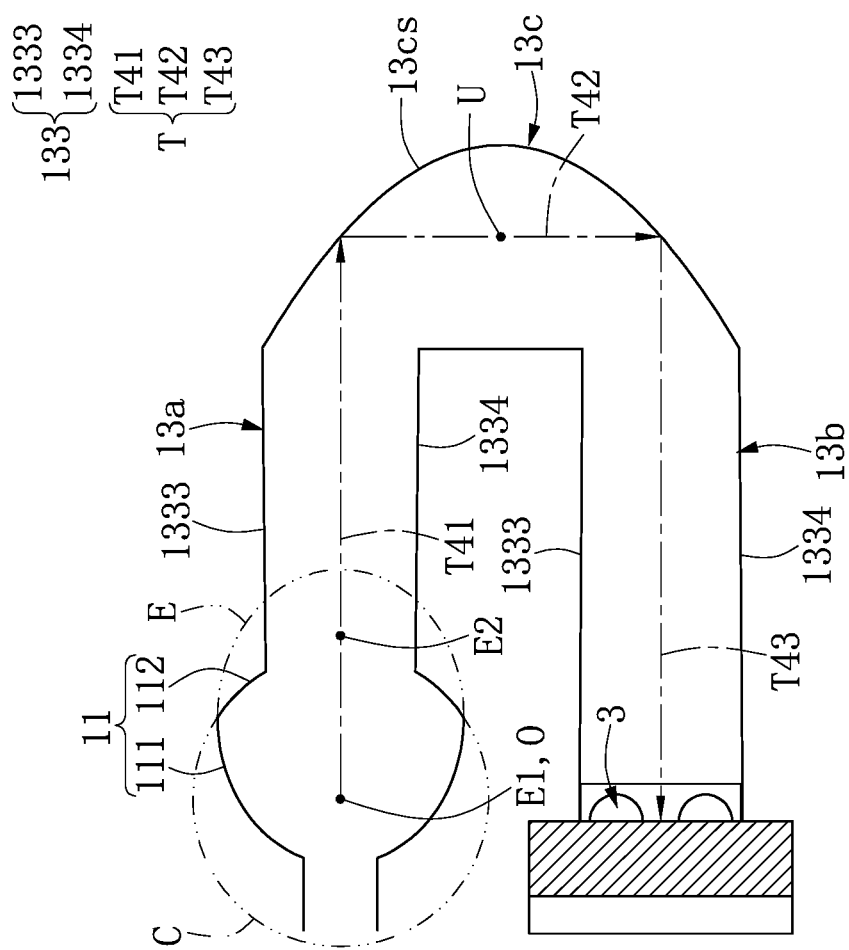
FIG. 22 depicts yet another path of projection of a light beam in the gas detection device according to the third embodiment of the instant disclosure.

Reference is made to FIG. 22. The details of the light path from the light emitting unit 21 to the reflecting surface 13cs of the turning portion 13c is described herein. Specifically, the projecting light beam T41 generated by the light emitting unit 21 can directly project onto the reflecting surface 13cs. Since the reflecting surface 13cs have a parabolic curvature, the projecting light beam T41 can be reflected by the reflecting surface 13cs for forming a reflecting light beam T42 passing through the focus point U of the reflecting surface 13cs. The reflecting light beam T42 can be reflected by the reflecting surface for forming a receiving light beam T43 projected onto the optical sensing unit 31 and received by the optical sensing unit 31.

Figure 23:
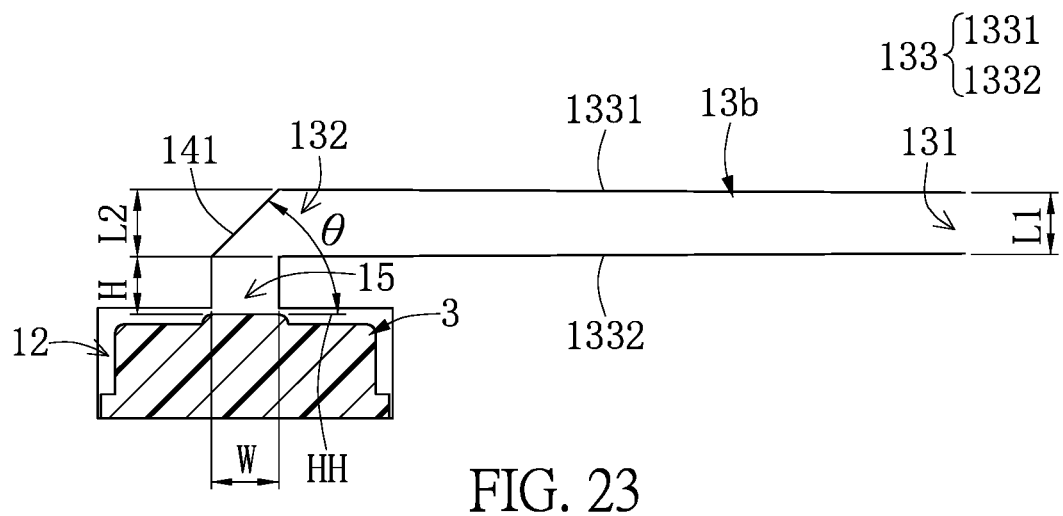
FIG. 23 is a sectional side schematic view taken along line XXIII-XXIII in FIG. 15.
Figure 24:
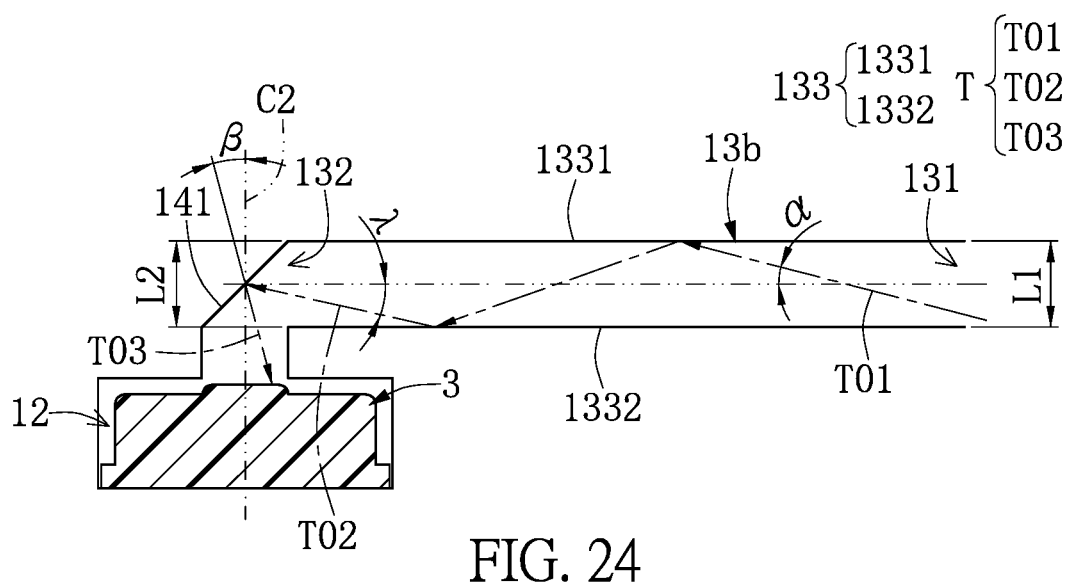
FIG. 24 is a schematic view showing the projection of light in a second sampling space.
Figure 25:
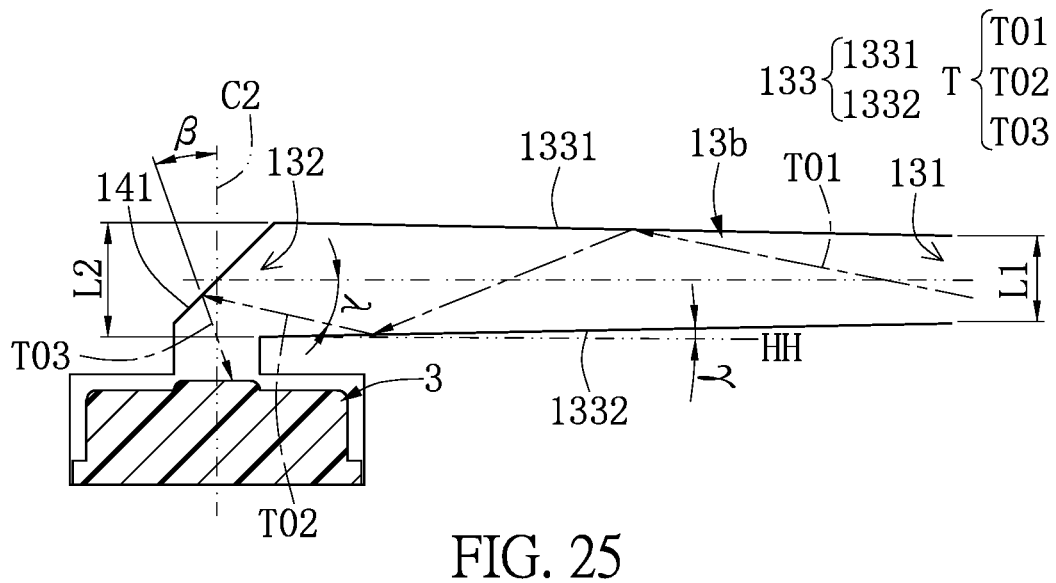
FIG. 25 is another schematic view showing the projection of light in the second sampling space.

Next, the light path in the second sampling chamber 13b is described in accompaniment with FIG. 23 to FIG. 25. Specifically, in the third embodiment of the instant disclosure, the chamber module 1 includes a light-guiding portion 14 disposed between the sampling chamber 13 and the receiving chamber 12. The light-guiding portion 14 can have a light-guiding surface 141 for reflecting the light beam T generated by the light emitting unit 21 to the optical sensing unit 31. In addition, the chamber module 1 can further include an open slot 15. The open slot 15 can be connected between the light-guiding portion 14 and the receiving chamber 12. Therefore, the light beam T generated by the light emitting unit 21 can be projected onto the optical sensing unit 31 by the light emitting unit 21 in a substantially L shape.

Reference is made to FIG. 23. The light-guiding surface 141 of the light-guiding portion 14 can incline relative to a horizontal axis HH at a predetermined angle θ ranging between 30 and 60 degrees. Alternatively, the light-guiding surface 141 of the light-guiding portion 14 inclines at a predetermined angle θ ranging from 30 to 60 degrees relative to the first surface 1331 or the second surface 1332 of the optical sensing unit 31. Preferably, the predetermined angle θ can be 45 degrees. In addition, it should be noted that the other features relative to the light-guiding portion 14 and the open slot 15 are similar to that of the previous embodiments and are not reiterated herein.

Reference is made to FIG. 24 and FIG. 25. In the third embodiment, the first surface 1331 and the second surface 1332 of the second sampling chamber 13b can be parallel to each other or not parallel to each other. As shown in FIG. 24, the second predetermined distance L2 is equal to the first predetermined distance L1, and the cross section of the first opening 131 is equal to the cross section of the second opening 132. As shown in FIG. 25, the first predetermined distance L1 and the second predetermined distance L2 are different, and the second predetermined distance L2 is larger than the first predetermined distance L1.

Specifically, as shown in FIG. 24 and FIG. 25, the second sampling chamber 13b has a first surface 1331 and a second surface 1332. The second sampling chamber 13b has a first opening 131 and a second opening 132 corresponding to the first opening 131. The first opening 131 is connected to the turning portion 13c, and the second opening 132 is connected to the receiving chamber 12. The first surface 1331 and the second surface 1332 of the first opening 131 has a first predetermined distance L1, and the first surface 1331 and the second surface 1332 of the second opening 132 has a second predetermined distance L2. The second predetermined distance L2 is larger than the first predetermined distance L1. In other words, the cross section of the first opening 131 is smaller than the cross section of the second opening 132 for increasing the infrared energy that is able to be received by the optical sensing unit 31. It should be noted that the light path in the second sampling chamber 13b shown in FIG. 24 and FIG. 25 are similar to that in the previous embodiment such as those described related to FIG. 9 and FIG. 10. In other words, the light in the second sampling chamber 13b of the gas detection device Q provided by the third embodiment also complies with the following equation: $\lambda=\alpha-2\gamma N$, in which $\alpha$ is the projecting angle, $\gamma$ is the incident angle, $\gamma$ is the inclined angle, and N is the time of reflection.

Figure 26:
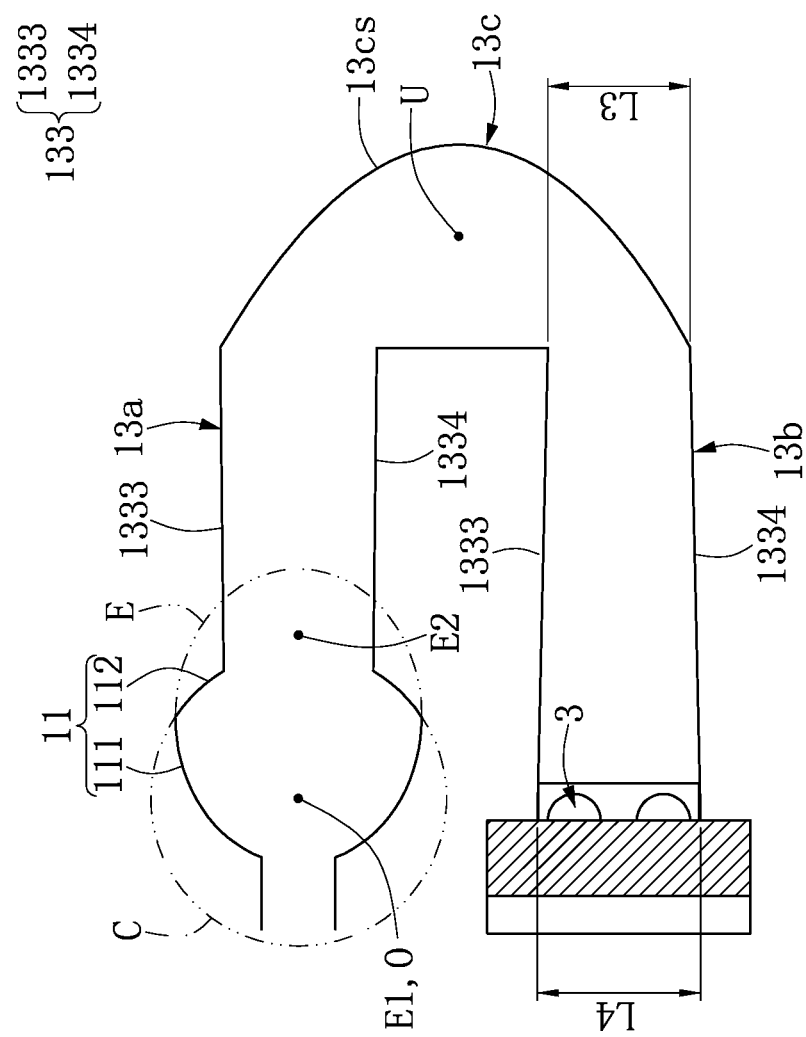
FIG. 26 is yet another schematic view showing the projection of light in the second sampling space.

Reference is made to FIG. 26 and FIG. 14. In other implementations, the third surface 1333 and the fourth surface 1334 opposite to the third surface 1333 of the second sampling chamber 13b can be not parallel to each other. Specifically, the third surface 1333 and the fourth surface 1334 of the first opening 131 can have a third predetermined distance L3 therebetween, the third surface 1333 and the fourth surface 1334 of the second opening 132 can have a fourth predetermined distance L4 therebetween. The fourth predetermined distance L4 is larger than the third predetermined distance L3. Therefore, based on the above feature, the infrared energy that is able to be received by the optical sensing unit 31 can be increased. Furthermore, in other embodiments, the third surface 1333 of the first sampling chamber 13a and the fourth surface 1334 opposite to the third surface 1333 can be not parallel to each other. Therefore, the light path can be changed, thereby increasing the infrared energy received by the optical sensing unit 31.

Figure 27:
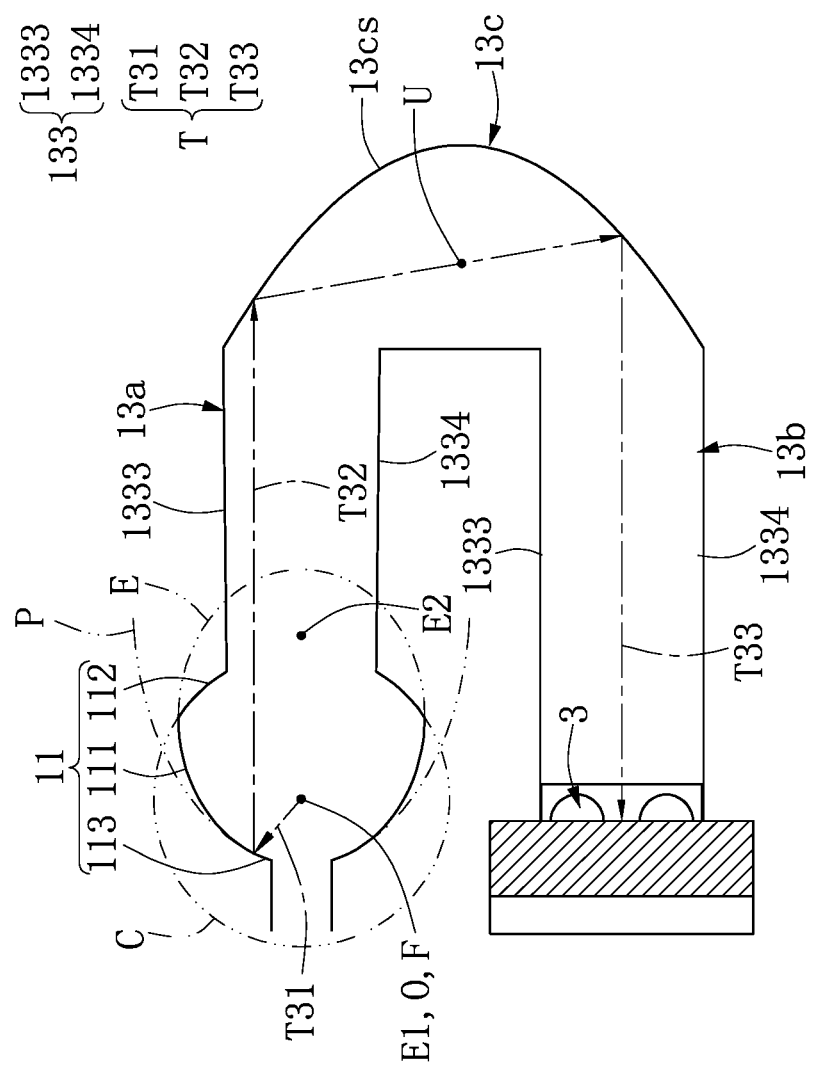
FIG. 27 is a schematic view showing the projection of light of the gas detection device including the third reflecting structure in the third embodiment of the instant disclosure.

Reference is made to FIG. 27. FIG. 27 to FIG. 20 to FIG. 22, the condensing chamber 11 of the embodiment shown in FIG. 27 further includes a third reflecting structure 113 such as that described in the first embodiment. Specifically, in the third embodiment, the light beam T generated by the light emitting module 2 further includes a third projecting light beam T31 projected onto the third reflecting structure 113. The third projecting light beam T31 can be reflected by the third reflecting structure 113 for forming a fourth reflecting light beam T32 projected onto the reflecting surface 13cs of the turning portion 13c, and the fourth reflecting light beam T32 can be reflected by the reflecting surface 13cs for forming a third receiving light beam T33 projected onto the optical sensing unit 31 and received by the optical sensing unit 31. Preferably, the reflecting surface 13cs can be a curved surface with a parabolic curvature, and hence, the fourth reflecting light beam T32 projected onto the reflecting surface 13cs can first pass through the focus point U of the reflecting surface 13cs and then project onto the reflecting surface 13cs for forming the third receiving light beam T33 projected onto the optical sensing unit 31 and received by the optical sensing unit 31.

It should be noted that the structure of the second sampling chamber 13b of the third embodiment is similar to the sampling chamber of the first embodiment, and the implementations in the first and second embodiments can be applied to the third embodiment.

Fourth Embodiment

Figure 28:
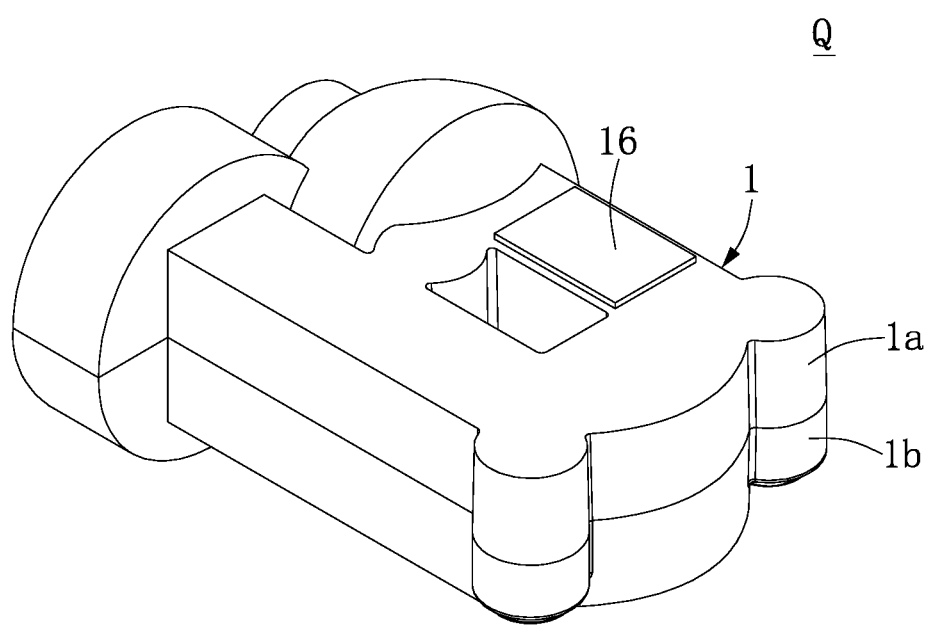
FIG. 28 is a three-dimensional assembly schematic view of a gas detection device of a fourth embodiment of the instant disclosure.
Figure 29:
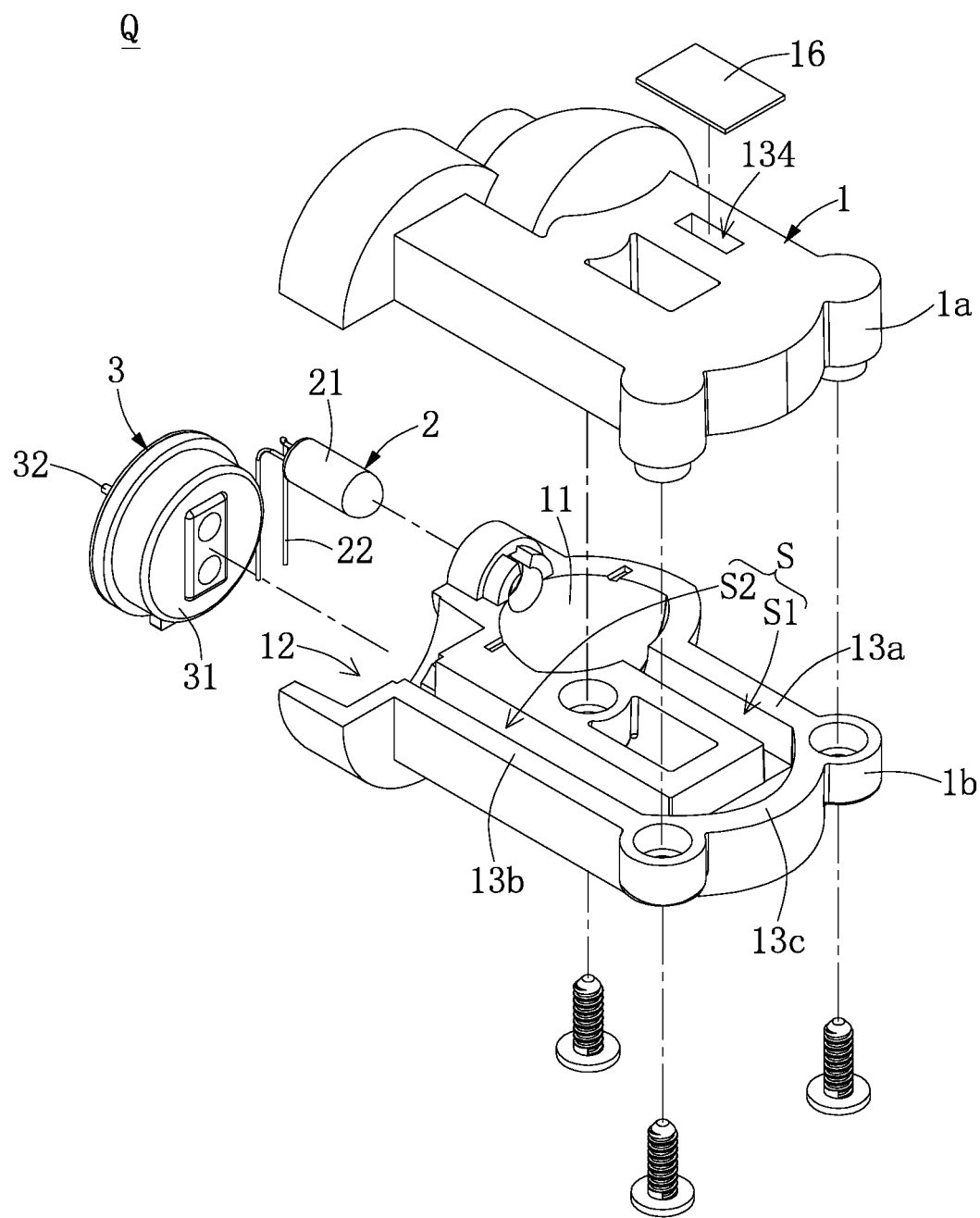
FIG. 29 is a three-dimensional exploded schematic view of a gas detection device of the fourth embodiment of the instant disclosure.
Figure 30:
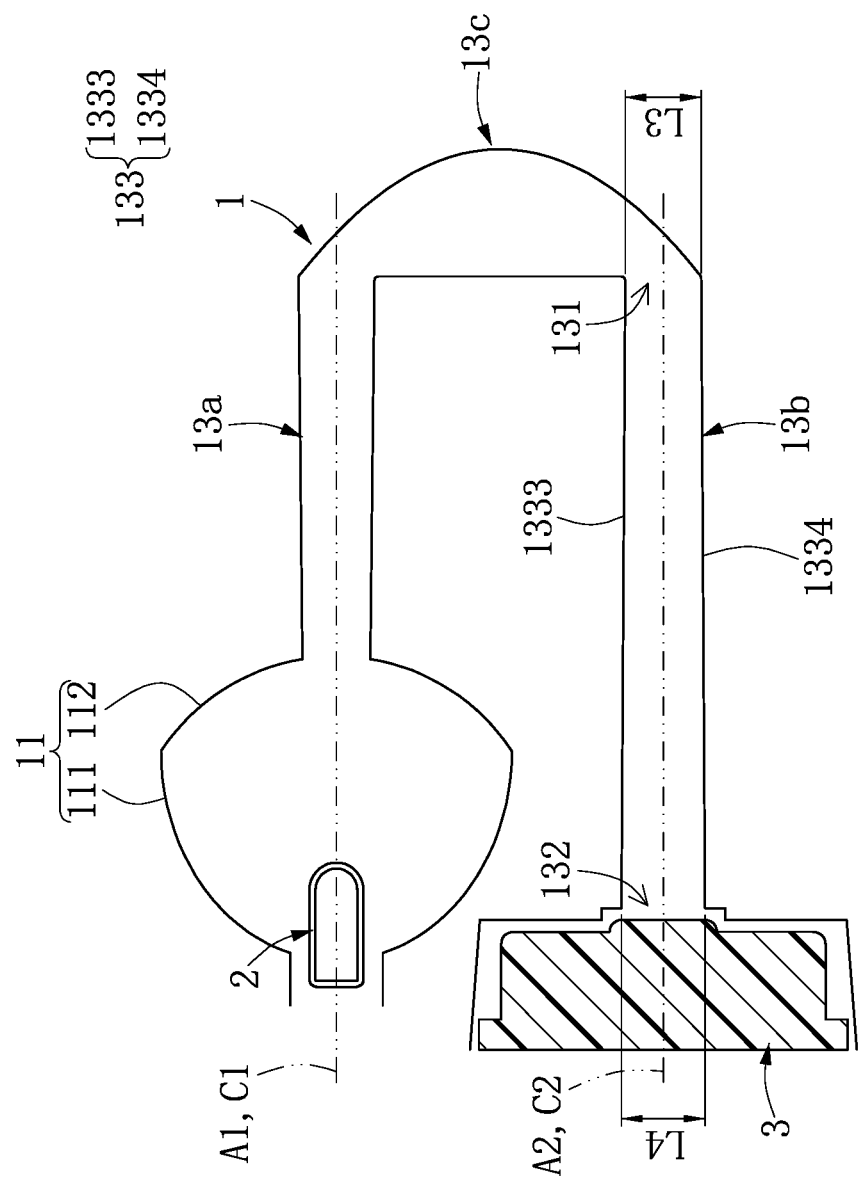
FIG. 30 is a schematic view showing the internal structure of a gas detection device of the fourth embodiment of the instant disclosure.

Reference is made to FIG. 28 to FIG. 30. Comparing FIG. 28 to FIG. 15, the main difference between the fourth embodiment and the second embodiment is that the receiving chamber 12 in the gas detection device Q provided by the fourth embodiment can have different shapes. In addition, the condensing chamber 11 can only have a first reflecting structure 111 and a second reflecting structure 112, and the curvature of the first reflecting structure 111 is different from that of the second reflecting structure 112. The third reflecting structure 113 is optionally disposed. In addition, in the fourth embodiment, the chamber module 1 can be designed to be without the light-guiding portion 14 and the open slot 15. Therefore, the light beam T generated by the light emitting unit 21 is directly reflected by the reflecting surface 13cs of the turning portion 13c and projected onto the optical sensing unit 31. In other words, the light emitting module 2 can have a first central axis C1 passing through the light source center (not shown) of the light emitting unit 21. The optical sensing module 3 can have a second central axis C2 passing through the center of the optical sensing module 3 for receiving light. It should be noted that other structural features of the gas detection device Q provided by the fourth embodiment are similar to those of the previous embodiments, and are not reiterated herein.

Figure 31:
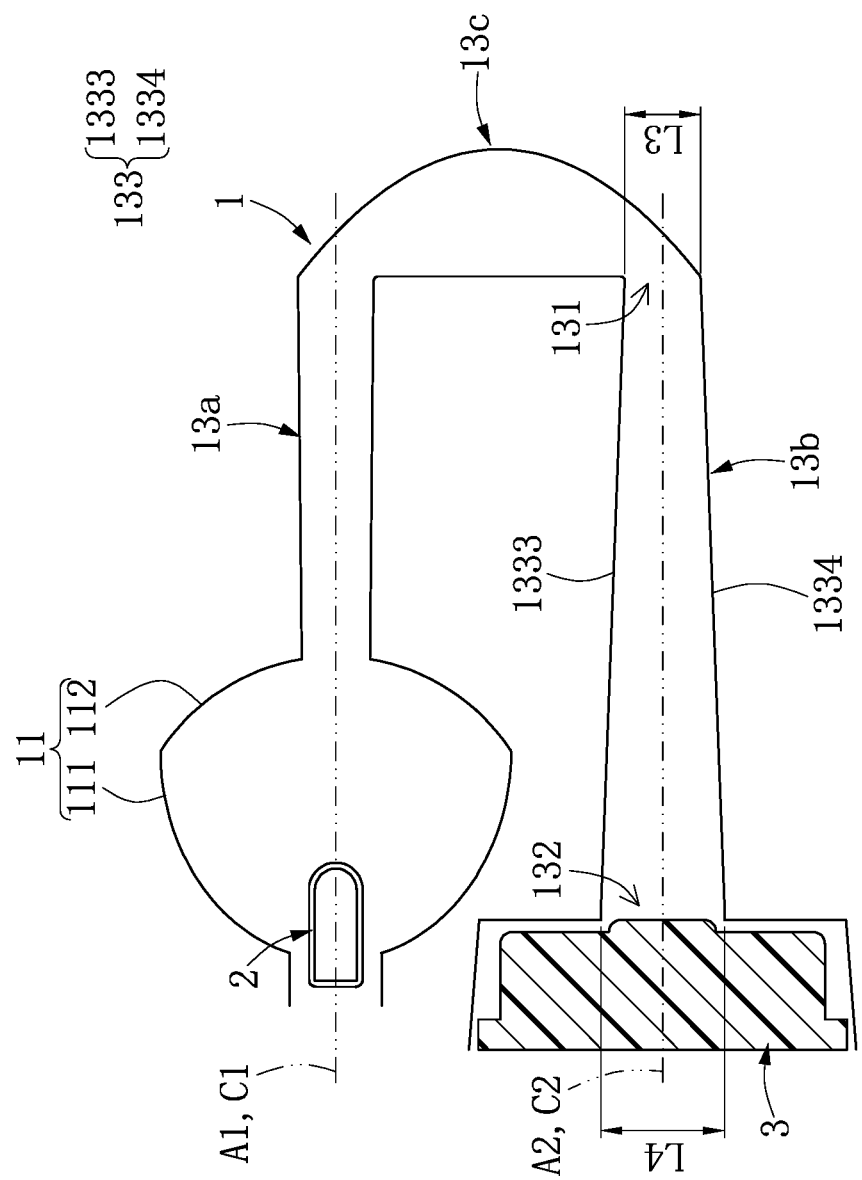
FIG. 31 is another schematic view showing the internal structure of a gas detection device of the fourth embodiment of the instant disclosure.

Reference is made to FIG. 30 and FIG. 31. The second sampling chamber 13b has a third surface 1333 and a fourth surface 1334. The second sampling chamber 13b has a first opening 131 and a second opening 132 corresponding to the first opening 131. The first opening 131 is connected to the turning portion 13c, and the second opening 132 is connected to the receiving chamber 12. The third surface 1333 and the fourth surface 1334 of the first opening 131 have a third predetermined distance L3 therebetween, and the third surface 1333 and the fourth surface 1334 of the second opening 132 have a fourth predetermined distance L4 therebetween. The fourth predetermined distance L4 can be larger than or equal to the third predetermined distance L3. In other words, the cross section of the first opening 131 can be smaller than or equal to the cross section of the second opening 132 for increasing the infrared energy that can be received by the optical sensing unit 31.

Fifth Embodiment

Reference is made to FIG. 32. Compared FIG. 32 to FIG. 20, the sampling chamber 13 in the gas detection device Q provided by fifth embodiment has a different shape. In other words, the first sampling chamber 13a, the second sampling chamber 13b and the turning portion 13c can be arranged in L-shape.

In addition, it should be noted that other structural features of the gas detection device provided by the fifth embodiment are similar to those of the previous embodiment, and the implementations of the previous embodiments can be applied to the fifth embodiment.

Effectiveness of the Instant Disclosure

The gas detection device Q provided by the embodiments of the instant disclosure includes the technical features of "the condensing chamber 11 has a first reflecting structure 111, a second reflecting structure 112 connected to the first reflecting structure 111, and a third reflecting structure 113 connected to the first reflecting structure 111, in which the first reflecting structure 111 is disposed between the second reflecting structure 112 and the third reflected structure 113" or "the sampling chamber 13 includes a first sampling chamber 13a connected to the condensing chamber 11, a second sampling chamber 13b connected to the receiving chamber 12 and a turning portion 13c connected between the first sampling chamber 13a and the second sampling chamber 13b, in which the turning portion 13c has a reflecting surface 13cs thereon", and hence, the light-condensing efficiency of the chamber module 1 can be increased, and the size of the gas detection device Q can be reduced.

The above-mentioned descriptions represent merely the exemplary embodiment of the present disclosure, without any intention to limit the scope of the instant disclosure thereto. Various equivalent changes, alterations or modifications based on the claims of the instant disclosure are all consequently viewed as being embraced by the scope of the instant disclosure.

What is claimed is:

1. A gas detection device, comprising:
a chamber module including a condensing chamber, a receiving chamber and a sampling chamber connected between the condensing chamber and the receiving chamber, wherein the condensing chamber has a first reflecting structure, a second reflecting structure connected to the first reflecting structure and a third reflecting structure connected to the first reflecting structure, wherein the first reflecting structure is disposed between the second reflecting structure and the third reflecting structure;
a light emitting module disposed on the condensing chamber and including a light emitting unit, wherein the light emitting unit corresponds to the condensing chamber; and
an optical sensing module including an optical sensing unit disposed in the receiving chamber;
wherein a curvature of the first reflecting structure, a curvature of the second reflecting structure and a curvature of the third reflecting structure are different from each other;
wherein the first reflecting structure has a first focus point and a second focus point corresponding to the first focus point, the second reflecting structure has a central point, and the third reflecting structure has a focus point, the first focus point, the central point and the focus point being disposed corresponding to each other;
wherein the light emitting unit corresponds to the first focus point, the central point and the focus point.

2. The gas detection device according to claim 1, wherein the light emitting unit is disposed on the first focus point, the central point and the focus point.

3. The gas detection device according to claim 1, wherein the first reflecting structure has an elliptical curved surface, the second reflecting structure has a circular curved surface, and the third reflecting structure has a parabolic curved surface.

4. The gas detection device according to claim 1, wherein the sampling chamber includes a first sampling chamber connected to the condensing chamber, a second sampling chamber connected to the receiving chamber, and a turning portion connected between the first sampling chamber and the second sampling chamber.

5. The gas detection device according to claim 4, wherein the first sampling chamber, the second sampling chamber and the turning portion are arranged in U-shape.

6. The gas detection device according to claim 1, wherein the sampling chamber has a first opening and a second opening corresponding to the first opening, the first opening being connected to the condensing chamber, the second opening being connected to the receiving chamber, and a cross section of the first opening being smaller than a cross section of the second opening.

7. The gas detection device according to claim 1, wherein the sampling chamber has a first surface and a second surface, the sampling chamber having a first opening and a second opening corresponding to the first opening, the first opening being connected to the condensing chamber, the second opening being connected to the receiving chamber, the first surface and the second surface of the first opening having a first predetermined distance therebetween, the first surface and the second surface of the second opening having a second predetermined distance therebetween, and the second predetermined distance being larger than the first predetermined distance.

8. The gas detection device according to claim 7, wherein the chamber module further includes a light guiding portion disposed between the sampling chamber and the receiving chamber, the second surface adjacent to the second opening and the optical sensing unit having a predetermined height therebetween, the predetermined height and the second predetermined distance complying with the following equation: $(0.8*L2) \leq H \leq (3*L2)$, wherein H is the predetermined height and L2 is the second predetermined distance.

9. The gas detection device according to claim 1, wherein the sampling chamber includes a first opening, a second opening corresponding to the first opening, a first surface and a second surface corresponding to the first surface, the first opening being connected to the condensing chamber, the second opening being connected to the receiving chamber, the first surface and the second surface being disposed between the first opening and the second opening, the first surface and the second surface being arranged to be not parallel to each other.

10. The gas detection device according to claim 1, wherein the chamber module further includes a guiding portion disposed between the sampling chamber and the receiving chamber, the light guiding portion having a light guiding surface, the light guiding surface inclining a predetermined angle ranging from 30 to 60 degrees relative to a horizontal axis.

11. The gas detection device according to claim 1, wherein the chamber module further includes a light guiding portion disposed between the sampling chamber and the receiving chamber and an open slot, the open slot being connected between the light guiding portion and the receiving chamber, the sampling chamber having a first surface and a second surface, the open slot having a predetermined width, the second surface and the optical sensing unit having a predetermined height therebetween, the predetermined width and the predetermined height complying with the following equation: $(0.8*W) \leq H \leq (3*W)$, wherein H is the predetermined height and W is the predetermined width.

12. The gas detection device according to claim 1, wherein the light emitting module is an infrared light emitter and the optical sensing module is an infrared light sensor.

13. The gas detection device according to claim 1, wherein the first reflecting structure has a first focus point and a second focus point corresponding to the first focus point, a light beam generated by the light emitting module including a first projecting light beam projected onto the first reflecting structure, a second projecting light beam projected onto the second reflecting structure and a third projecting light beam projected onto the third reflecting structure, wherein the first projecting light beam is reflected by the first reflecting structure for forming a first reflecting light beam projected onto the second focus point, the first reflecting light beam cooperating with the sampling chamber for forming a first receiving light beam projected onto the optical sensing unit and received by the optical sensing unit, wherein the second projecting light beam is reflected by the second reflecting structure for forming a second reflecting light beam projected onto the first reflecting structure, the second reflecting light beam being reflected by the first reflecting structure for forming a third reflecting light beam projected onto the second focus point, the third reflecting light beam cooperating with the sampling chamber for forming a second receiving light beam projected onto the optical sensing unit and received by the optical sensing unit, wherein the third projecting light beam is reflected by the third reflecting structure for forming a third receiving light beam projected onto the optical sensing unit and received by the optical sensing unit.

* * * * *